(12) United States Patent
Cha et al.

(10) Patent No.: US 8,332,026 B2
(45) Date of Patent: Dec. 11, 2012

(54) METHOD OF ANALYZING BODY COMPOSITION WITH MEASUREMENT OF VOLTAGE SIGNALS AT MULTIPLE POSITIONS OF BODY

(75) Inventors: Ki Chul Cha, Seoul (KR); Chang Ryoul Yang, Uiwang (KR)

(73) Assignee: Biospace Co., Ltd. (KR)

( * ) Notice: Subject to any disclaimer, the term of this patent is extended or adjusted under 35 U.S.C. 154(b) by 277 days.

(21) Appl. No.: 12/702,244

(22) Filed: Feb. 8, 2010

(65) Prior Publication Data

US 2010/0249641 A1  Sep. 30, 2010

(30) Foreign Application Priority Data

Mar. 24, 2009 (KR) .................. 10-2009-0025136
Mar. 30, 2009 (KR) .................. 10-2009-0027111

(51) Int. Cl.
*A61B 5/05* (2006.01)

(52) U.S. Cl. ....................... 600/547; 600/309

(58) Field of Classification Search .................... 600/547
See application file for complete search history.

(56) References Cited

U.S. PATENT DOCUMENTS

| | | |
|---|---|---|
| 3,851,641 A | 12/1974 | Toole et al. |
| 3,871,359 A | 3/1975 | Pacela |
| 3,971,365 A | 7/1976 | Smith |
| 4,008,712 A | 2/1977 | Nyboer |
| 4,116,231 A | 9/1978 | Matsuo |
| 4,377,170 A | 3/1983 | Carim |
| 4,450,527 A | 5/1984 | Sramek |
| 4,557,271 A | 12/1985 | Stoller et al. |
| 4,733,670 A | 3/1988 | Hays et al. |
| 4,793,362 A | 12/1988 | Tedner |
| 4,794,934 A | 1/1989 | Motoyama et al. |
| 4,805,621 A | 2/1989 | Heinze et al. |
| 4,807,638 A | 2/1989 | Sramek |
| 4,870,578 A | 9/1989 | Vysin et al. |
| 4,895,163 A | 1/1990 | Libke et al. |
| 4,911,175 A | 3/1990 | Shizgal |
| 4,919,145 A | 4/1990 | Marriott |
| 4,947,862 A | 8/1990 | Kelly |

(Continued)

FOREIGN PATENT DOCUMENTS

JP  56-040126 A  4/1981

(Continued)

OTHER PUBLICATIONS

Baumgartner, et al., Estimation of body composition from bioelectric impedance of body segments, Am J Clin Nutr 1989; vol. 50, pp. 221-226 (1980).

(Continued)

*Primary Examiner* — Max Hindenburg
*Assistant Examiner* — Renee Danega
(74) *Attorney, Agent, or Firm* — Knobbe Martens Olson & Bear, LLP

(57) ABSTRACT

A method of analyzing a composition of a human body having a plurality of body segments is disclosed. The method can include applying a current signal to a body. The method can further include simultaneously measuring a plurality of voltage signals from a plurality of measuring positions of the body during a predetermined period, and processing at least two of the plurality of voltage signals to determine a composition parameter of a body segment so as to assess or analyze composition of the body.

18 Claims, 13 Drawing Sheets

U.S. PATENT DOCUMENTS

| | | | |
|---|---|---|---|
| 5,063,937 | A | 11/1991 | Ezenwa et al. |
| 5,086,781 | A | 2/1992 | Bookspan |
| 5,103,828 | A | 4/1992 | Sramek |
| 5,178,154 | A | 1/1993 | Ackmann et al. |
| 5,203,344 | A | 4/1993 | Scheltinga et al. |
| 5,280,429 | A | 1/1994 | Withers |
| 5,309,917 | A | 5/1994 | Wang et al. |
| 5,335,667 | A * | 8/1994 | Cha et al. .................. 600/547 |
| 5,372,141 | A | 12/1994 | Gallup et al. |
| 5,415,176 | A | 5/1995 | Sato et al. |
| 5,720,296 | A | 2/1998 | Cha |
| 6,256,532 | B1 | 7/2001 | Cha |
| 6,400,983 | B1 | 6/2002 | Cha |
| 6,725,089 | B2 * | 4/2004 | Komatsu et al. ............ 600/547 |
| 8,099,250 | B2 | 1/2012 | Essex et al. |
| 2002/0062090 | A1 | 5/2002 | Chai et al. |
| 2004/0015058 | A1 * | 1/2004 | Besson et al. ............... 600/301 |
| 2006/0004300 | A1 | 1/2006 | Kennedy |
| 2008/0270051 | A1 | 10/2008 | Essex et al. |
| 2010/0168530 | A1 * | 7/2010 | Chetham et al. ............ 600/301 |

FOREIGN PATENT DOCUMENTS

| | | |
|---|---|---|
| JP | 60-053029 U | 4/1985 |
| JP | 60-123739 A | 7/1985 |
| JP | 62-000324 A | 1/1987 |
| JP | 62-169023 A | 7/1987 |
| JP | 04-218729 A | 8/1992 |
| JP | 07-012635 A | 1/1995 |
| JP | 07-079938 A | 3/1995 |
| JP | 07-100122 A | 4/1995 |
| WO | WO 2008-064426 A1 | 6/2008 |

OTHER PUBLICATIONS

Biggs et al., Electrical resistivity of the upper arm and leg yields good estimates of whole body fat, Institute of Physics Publishing, Physiol. Meas. 2001, vol. 22, pp. 365-376.

Chumlea, et al., Specific resistivity used to estimate fat-free mass from segmental body measures of bioelectric impedance 1-3, Am J Clin Nutr 1988; vol. 48, pp. 7-15.

Cordain, et al., Body Composition Determination in Children Using Bioelectrical Impedance, Growth, Development & Aging, 1988, vol. 52, No. 1, pp. 37-40.

Deurenberg et al., Assessment of body composition by bioelectrical impedance in a population aged >60y, Am J Clin Nutr 1990, vol. 51, pp. 3-6.

Fuller, et al., Potential Use of Bioelectrical Impedance of the "Whole Body" and of Body Segments for the Assessment of Body Composition: Comparison with Densitometry and Anthropometry, European Journal of Clinical Nutrition, 1989, vol. 43, pp. 779-791.

Hodgdon & Fitzgerald, Validity of Impedance Predictions at Various Levels of Fatness, Bioelectrical Estimation of Body Composition, pp. 281-298.

Hoffer, et al., Correlation of whole-body impedance with total body water volume, Journal of Applied Physiology, Oct 1969, vol. 27, No. 4, pp. 531-534.

Jenin, et al., Determination of Body Fluid Compartment by Electrical Impedance Measurements, Aviation, Space and Environmental Medicine, Feb. 1975, vol. 46, No. 1, pp. 152-155.

Kushner, Bioelectrical Impedance Analysis: A Review of Principles and Applications, Journal of the American College of Nutrition, 1992, vol. 11, No. 2, pp. 199-209.

Lukaski, et al., Assessment of fat free mass using bio-electrical impedance measurements of the human body, Am. J. Clin. Nutr., 1985, vol. 41, pp. 810-817.

Lukaski, et al., Estimation of Body Fluid Volumes Using Tetrapolar Bioelectrical Impedance Measurements, Aviation, Space, & Environmental Medicine, Dec. 1988, pp. 1163-1169.

Lukaski, et al., Validation of tetrapolar bioelectrical impedance method to assess human body composition, J. Appl. Physiol. 1986, vol. 60, No. 4, pp. 1327-1332.

Lukaski, Methods for the assessment of human body composition: traditional and new, Am J Clin Nutr 1987; vol. 46, pp. 537-556.

Organ, et al., Segmental bioelectrical impedance analysis: theory and application of a new technique, J. Appl. Physiol., 1994, vol. 77, No. 1, pp. 98-112.

Patterson, Body Fluid Determinations Using Multiple Impedance Measurements, IEEE Engineering in Medicine and Biology Magazine, Mar. 1989, pp. 16-18.

Patterson, Measurement of body fluid volume change using multisite impedance measurements, Medical & Biological Engineering & Computing, Jan. 1988, pp. 33-36.

RJL Systems, Body Composition Bioelectrical Impedance Analyzers (BIA), Quantum Series Product Catalog, Jan. 1, 2009—9 pages.

RJL Systems, The history of Bioelectrical Impedance Analysis (BIA), http://www.rjlsystems.com/about_bia/bia_history/—2 pages.

Schols, et al., Body composition by bioelectrical-impedance analysis compared with deuterium dilution and skinfold anthropometry in patients with chronic obstructive pulmonary disease, Am J Clin Nutr 1991; vol. 53, pp. 421-424.

Segal, et al., Lean body mass estimation by bioelectrical impedance analysis: a four-site cross-validation study, Am J. Clin Nutr, 1988; vol. 47, pp. 7-14.

Spangler, Best Alternative to a Negotiated Agreement (BATNA), http://beyondintractability.org/essay/batna/, Jun. 2003—6 pages.

* cited by examiner

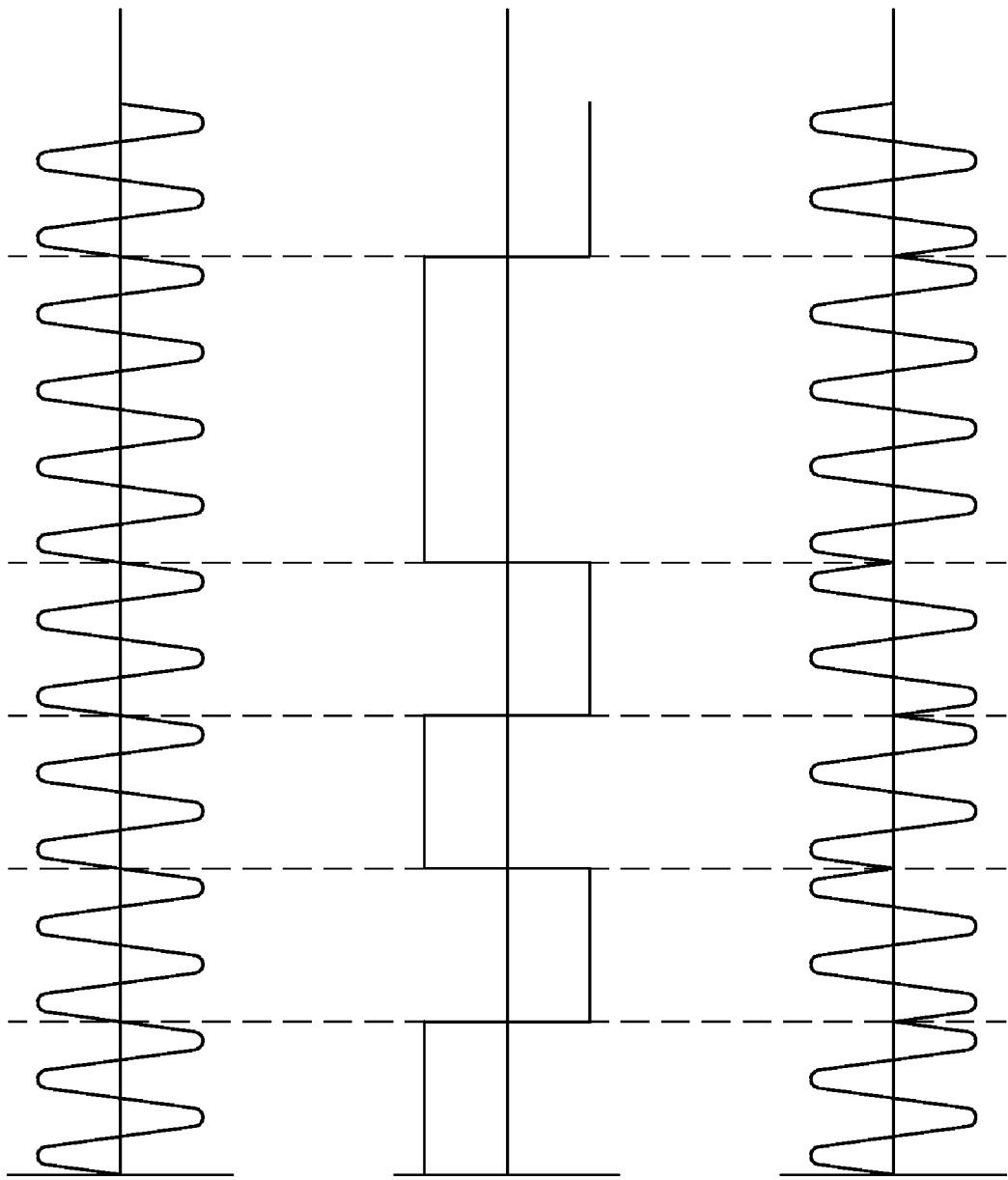

METHOD OF ANALYZING BODY COMPOSITION WITH MEASUREMENT OF VOLTAGE SIGNALS AT MULTIPLE POSITIONS OF BODY

CROSS-REFERENCE TO RELATED APPLICATION

This application claims priority to and the benefit of Korean Patent Application Nos. 10-2009-0025136 filed Mar. 24, 2009 and 10-2009-0027111 filed Mar. 30, 2009, the disclosures of which are incorporated herein by reference in their entirety. This application is related to and incorporates herein by reference the entire contents of the following concurrently filed applications:

| Title | Atty. Docket No. | Filing Date | Application No. |
|---|---|---|---|
| METHOD OF ANALYZING BODY COMPOSITION WITH MEASUREMENT OF VOLTAGE SIGNALS AT MULIPLE POSITIONS OF BODY | BSPACE.001AUS | | |
| METHOD OF ANALYZING BODY COMPOSITION WITH MEASUREMENT OF VOLTAGE SIGNALS AT MULIPLE POSITIONS OF BODY | BSPACE.001AUS3 | | |

BACKGROUND

1. Field

The present disclosure relates to body composition analysis using voltage signals measured at multiple positions of the body.

2. Discussion of Related Technology

Generally, body composition is used to describe which percentage of a human body is water, fat, bone, muscle, or the like. Analysis of body composition provides benefits. For example, in physical fitness, information of body composition of a person can be used for establishing a personalized exercise plan. For overweight people, such information can provide a visual warning to lead to formation of a personal diet goal. Physicians can use body composition information to treat a patient. Bioelectrical impedance analysis is one of many ways to estimate body composition. However, there is still a need to provide accurate analysis of body composition.

The foregoing discussion in this section is to provide general background information, and does not constitute an admission of prior art.

SUMMARY

One aspect of the invention provides a method of assessing composition of a body. The method comprises: establishing contact of a first extremity current electrode with a first extremity; establishing contact of a first extremity voltage electrode A and a first extremity voltage electrode B with the first extremity; establishing contact of a second extremity current electrode with a second extremity; establishing contact of a second extremity voltage electrode A and a second extremity voltage electrode B with the second extremity; establishing contact of a third extremity current electrode with a third extremity; establishing contact of a third extremity voltage electrode A and a third extremity voltage electrode B with the third extremity; establishing contact of a fourth extremity current electrode with a fourth extremity; establishing contact of a fourth extremity voltage electrode A and a fourth extremity voltage electrode B with the fourth extremity; applying a current signal between the first extremity current electrode and the second extremity current electrode; applying another current signal between the third extremity current electrode and the fourth extremity current electrode; measuring voltages at the first extremity voltage electrode A, at the second extremity voltage electrode A, at the third extremity voltage electrode A, and at the fourth extremity voltage electrode A; measuring voltages at the first extremity voltage electrode B, at the second extremity voltage electrode B, at the third extremity voltage electrode B, and at the fourth extremity voltage electrode B; processing the measured voltages at the first extremity voltage electrode A, at the second extremity voltage electrode A, at the third extremity voltage electrode A, and at the fourth extremity voltage electrode A, which provides a first value representing impedance of a first one of a plurality of predetermined segments of the body; processing the measured voltages at the first extremity voltage electrode B, at the second extremity voltage electrode B, at the third extremity voltage electrode B, and at the fourth extremity voltage electrode B, which provides a second value representing impedance of a second one of the plurality of predetermined segments; and assessing composition of the body using the first and second values.

In the foregoing method, the other current signal between the third extremity current electrode and the fourth extremity current electrode may be applied simultaneously with applying a current signal between the first extremity current electrode and the second extremity current electrode. The voltages at the first extremity voltage electrode A, at the second extremity voltage electrode A, at the third extremity voltage electrode A, and at the fourth extremity voltage electrode A may be simultaneously measured. The first extremity may comprise a right arm and the second extremity comprises a right leg or a left leg. The current signal may be provided using a first current source, wherein the other current signal may be provided using a second current source, wherein the first current source and the second current source may be electrically decoupled. Processing the measured voltages at the first extremity voltage electrode A, at the second extremity voltage electrode A, at the third extremity voltage electrode A, and at the fourth extremity voltage electrode A may comprise obtaining a first voltage drop signal between two voltage electrodes selected from the first extremity voltage electrode A, the second extremity voltage electrode A, the third extremity voltage electrode A and the fourth extremity voltage electrode A; and computing a first value indicative of impedance between the two selected voltage electrodes using the first voltage drop signal and the current signal. Processing the measured voltages at the first extremity voltage electrode B, at the second extremity voltage electrode B, at the third extremity voltage electrode B, and at the fourth extremity voltage electrode B may comprise: obtaining a second voltage drop signal between two voltage electrodes selected from the first extremity voltage electrode B, the second extremity voltage electrode B, the third extremity voltage electrode B and the fourth extremity voltage electrode B; and computing a second value indicative of impedance between the two selected voltage electrodes using the second voltage drop signal and the other current signal.

Another aspect of the invention provides an apparatus for assessing composition of a body. The apparatus comprises: a first extremity current electrode for contacting a first extremity; a second extremity current electrode for contacting a second extremity; a third extremity current electrode for contacting a third extremity; a fourth extremity current electrode for contacting a fourth extremity; a first current source configured to provide a first current signal between the first extremity current electrode and the second extremity current electrode; a second current source configured to provide a second current signal between the third extremity current electrode and the fourth extremity current electrode; a first extremity voltage electrode A for contacting the first extremity; a second extremity voltage electrode A for contacting the second extremity; a third extremity voltage electrode A for contacting the third extremity; a fourth extremity voltage electrode A for contacting the fourth extremity; a voltage measuring circuit A configured to simultaneously measure voltages at the first extremity voltage electrode A, at the second extremity voltage electrode A, at the third extremity voltage electrode A, and at the fourth extremity voltage electrode A; a first extremity voltage electrode B for contacting the first extremity; a second extremity voltage electrode B for contacting the second extremity; a third extremity voltage electrode B for contacting the third extremity; a fourth extremity voltage electrode B for contacting the fourth extremity; a voltage measuring circuit B configured to simultaneously measure voltages at the first extremity voltage electrode B, at the second extremity voltage electrode B, at the third extremity voltage electrode B, and at the fourth extremity voltage electrode B; one or more processing circuits configure to process the measured voltages at the first extremity voltage electrode A, at the second extremity voltage electrode A, at the third extremity voltage electrode A, and at the fourth extremity voltage electrode A, which provides a first value representing impedance of a first one of a plurality of predetermined segments of the body; the one or more processing circuits further configured to process the measured voltages at the first extremity voltage electrode B, at the second extremity voltage electrode B, at the third extremity voltage electrode B, and at the fourth extremity voltage electrode B, which provides a second value representing impedance of a second one of the plurality of predetermined segments; and the one or more processing circuits further configured to assess composition of the body using the first and second values.

In the foregoing apparatus, the first extremity may comprise a right arm and the second extremity comprises a right leg or a left leg. The first current source and the second current source may be electrically decoupled. The voltage measuring circuit A and voltage measuring circuit B may be electrically decoupled. The one or more processing circuits may be further configured to obtain a first voltage drop signal between two voltage electrodes selected from the first extremity voltage electrode A, the second extremity voltage electrode A, the third extremity voltage electrode A and the fourth extremity voltage electrode A, and compute a first value indicative of impedance between the two selected voltage electrodes using the first voltage drop signal and the current signal, wherein the one or more processing circuits are further configured to obtain a second voltage drop signal between two voltage electrodes selected from the first extremity voltage electrode B, the second extremity voltage electrode B, the third extremity voltage electrode B and the fourth extremity voltage electrode B, and compute a second value indicative of impedance between the two selected voltage electrodes using the second voltage drop signal and the other current signal.

Still another aspect of the invention provides a method of analyzing composition of a body. The method comprises: establishing contact of current electrodes with four extremities, a first one of the current electrodes contacting a first extremity, a second one of the current electrodes contacting a second extremity, a third one of the current electrodes contacting a third extremity, a fourth one of the current electrodes contacting a fourth extremity; establishing contact of a first set of voltage measuring electrodes with the four extremities, each extremity contacting one of the first set of voltage measuring electrodes; establishing contact of a second set of voltage measuring electrodes with the four extremities, each extremity contacting one of the second set of voltage measuring electrodes; applying a first current signal between the first and second current electrodes using a first current source; simultaneously with applying of the first current signal, applying a second current signal between the third and fourth electrodes using a second current source which is electrically decoupled from the first current source; simultaneously measuring voltage signals from the first set of voltage measuring electrodes with a first voltage measuring circuit; simultaneously measuring voltage signals from the second set of voltage measuring electrodes with a second voltage measuring circuit, wherein the second voltage measuring circuit is electrically decoupled from the first voltage measuring circuit; and processing the measured voltage signals from the first set of voltage measuring electrodes to determine a composition parameter of a first portion of the body, and further processing the measured voltage signals from the second set of voltage measuring electrodes to determine a composition parameter of a second portion of the body, wherein the composition of the body is assessed using at least the determined composition parameters.

In the foregoing method, said processing may comprise: processing two voltage signals from the at least two voltage signals to determine a voltage drop signal; and determining the at least one composition parameter based on the voltage drop signal and the first current signal. The first current source comprises a first ground and the second current source comprises a second ground which is electrically decoupled from the first ground, wherein the voltage signals may be measured from the first set of voltage measuring electrodes with respect to the first ground, wherein the second set of voltage signals may be measured are measured from the second set of voltage measuring electrodes with respect to the second ground. The voltage measuring electrodes contacting the first extremity may be spaced from each other to be electrically decoupled from each other. The composition parameter of the first portion may comprise a value representing impedance of the first portion. The composition parameter of the first portion may comprise at least one selected from the group consisting of percentages of body water, body fat, bone, and muscle.

Still in the foregoing method, the first current signal may comprise a first sinusoidal signal having a first frequency, wherein the second current signal may comprise a second sinusoidal signal having a second frequency which is different from the first frequency. The second sinusoidal signal may be a harmonic of the first sinusoidal signal. The first current signal may represent at least two superimposed frequencies. The applying the first current signal may comprise generating a first modulated signal having a first waveform, wherein said applying the second current signal may comprise generating a second modulated signal having a second waveform substantially different from the first waveform. Each of said modulated signals may be generated using a phase-shifting keying (PSK) modulation scheme. The applying the first current signal may comprise: generating a first modulated signal having a first waveform; generating a second modulated signal having a second waveform substantially different from the first waveform; and combining the first and second modulated signals to form the first current signal.

Yet another aspect of the invention provides a method of assessing composition of a body comprising a trunk and four extremities attached thereto, the four extremities comprising first, second, third and fourth extremities. The method comprises: applying a first current signal between the first and second extremities; applying a second current signal between the third and fourth extremities; simultaneously measuring at least one voltage signal at a distal end portion of each of the four extremities; obtaining a first voltage drop signal between the distal end portion of one of the four extremities and the distal end portion of another of the four extremities; computing a first value indicative of impedance between the two distal end portions using the first voltage drop signal and the first current signal; obtaining a second voltage drop signal between the distal end portion of one of the four extremities and the distal end portion of another of the four extremities, wherein at least one of the two distal end portions used for obtaining the second voltage drop signal is not either of the two extremities used for obtaining the first voltage drop signal; and computing a second value indicative of impedance between the two distal end portions using the second voltage drop signal and the second current signal. In the foregoing method, the method may comprise assessing composition of the body using the first and second values. The second current signal is applied simultaneously with applying the first current signal.

A further aspect of the invention provides a method of analyzing composition of a body. The method comprises: establishing contact of current electrodes with four extremities, each extremity contacting at least one of the current electrodes; establishing contact of voltage measuring electrodes with the four extremities, each extremity contacting at least one of the voltage measuring electrodes; applying a first current signal between first and second extremities through a body via the current electrodes contacting the first and second extremities; simultaneously application of the first current signal, applying a second current signal between third and fourth extremities through the body via the current electrodes contacting the third and fourth extremities; simultaneously measuring voltage signals from the voltage measuring electrodes contacting the four extremities; and processing a first set of voltage signals among the measured voltage signals to determine a composition parameter of a first portion of the body based on the first set of voltage signals and the first current signal, and further processing a second set of voltage signals among the measured voltage signals to determine a composition parameter of a second portion of the body based on the second set of voltage signals and the second current signals, wherein the composition of the body is assessed using at least the determined composition parameters.

In the foregoing method, the voltage signals may be measured while the first and second current signals are applied. The first current signal may be applied using a first current source and the second current signal may be applied using a second current source which is decoupled from the first current source. The first set of voltage signals may be measured in response to the application of the first current signal. Processing the first set of voltage signals may comprise: selecting two voltage signals from the first set of voltage signals; and determining a voltage drop signal using the selected voltage signals; wherein the composition parameter of the first portion is determined based on the voltage drop signal and the first current signal. The composition parameter may comprise a value representing impedance of the first portion. The composition parameter may comprise at least one selected from the group consisting of percentages of body water, body fat, bone, and muscle.

Still in the foregoing method, the first current signal may comprise a first sinusoidal signal having a first frequency and a second sinusoidal signal having a second frequency which is distinguishable from the first frequency, wherein the first current signal represents superimposed frequencies. The second sinusoidal signal may be a harmonic of the first sinusoidal signal. The composition parameter of the first portion may comprise a first value representing impedance of the first portion with respect to the first frequency and a second value representing impedance of the first portion with respect to the second frequency. Processing may comprise: selecting two voltage signals from the first set of voltage signals; determining a voltage drop signal using the two voltage signals; and determining the first and second values based on the voltage drop signal and the first current signal. Processing the voltage drop signal may comprise: multiplying a signal having the first frequency to the voltage drop signal to obtain a multiplied signal; integrating the multiplied signal for a period to obtain an integrated value; and processing the integrated value to determine the first value.

Yet in the foregoing method, applying the first current signal may comprise generating a modulated signal to be applied. Applying the first current signal may comprise: generating a first modulated signal having a first waveform; generating a second modulated signal having a second waveform distinguishable from the first waveform; and combining the first and second modulated signals to form the first current signal. Each of said modulated signals may be generated using a phase-shifting keying (PSK) modulation scheme. The first current signal may represent a single frequency. Applying the first current signal may comprise generating a modulated signal representing the single frequency. The modulated signal may be generated using a phase-shifting keying (PSK) modulation scheme. The first extremity may be one arm of the body and the second extremity is one leg of the body. The portion of the body may comprise at least one selected from a right arm, a left arm, a right leg, a left leg and a trunk.

Still a further aspect of the invention provides a method of assessing composition of a body comprising a trunk and four extremities attached thereto, the four extremities comprising first, second, third and fourth extremities. The method comprises: applying a first current signal between the first and second extremities, the first current signal comprising a first frequency component in a first frequency; applying a second current signal between the third and fourth extremities, the second current signal comprising a second frequency component in a second frequency substantially different from the first frequency; measuring at least one voltage signal at a distal end portion of each of the four extremities; processing the at least one voltage signals to obtain a first value indicative of impedance of a first extremity with respect to the first frequency, further processing the at least one voltage signals to obtain a second value indicative of impedance of a second extremity with respect to the second frequency; and assessing composition of the body using the first and second values, wherein assessing does not use impedance of the first extremity with respect to the second frequency obtainable from processing of the at least one voltage signals.

In the foregoing method, assessing does not use impedance of the second extremity with respect to the first frequency obtainable from processing of the at least one voltage signals.

The first current signal may comprise a third frequency component in a third frequency which is substantially different from the first and second frequencies.

Yet a further aspect of the invention provides a method of analyzing composition of a body. The method comprises: providing a first current signal having a first frequency to a first current path through the body and between a first upper extremity and a first lower extremity; simultaneously with providing of the first current signal, providing a second current signal having a second frequency distinguishable from the first frequency to a second current path through the body and between a second upper extremity and a second lower extremity; measuring voltage signals from voltage measuring positions of the four extremities while the first and second current signals are applied, each extremity comprising at least one of the voltage measuring positions; processing the measured voltage signals to determine a first value representing impedance of a first body segment with respect to the first frequency and a second value representing impedance of a second body segment with respect to the second frequency.

In the foregoing method, the first body segment and the second body may be the same body segment. The first body segment and the second body segment may be different body segments. Each of the first body segment and the second body segment may be a segment selected from the group consisting of a trunk and four extremities.

Still in the foregoing method, the first body segment may be one of upper extremities, wherein said processing may comprise estimating a third value representing impedance of the other upper extremity with respect to the first frequency based on the first value. The third value may be estimated to be substantially same with the first value. Processing may comprise assessing composition of the body using the values representing impedance of the body segments. The at least one composition parameter may comprise at least one selected from the group consisting of percentages of body water, body fat, bone, and muscle. Processing may comprises: processing two voltage signals from the plurality of voltage signals to determine a voltage drop signal; and determining the first value based on the voltage drop signal and the first current signal.

Yet in the foregoing method, the first current signal may be applied using a first current source, wherein the second current signal may be applied using a second current source which is electrically decoupled from the first current source. The first current signal may represent a single frequency. Applying the at least one current signal may comprise generating a modulated signal. The modulated signal may be generated using a phase-shifting keying (PSK) modulation scheme. The first current signal may be a combined signal of two or more sinusoidal signals and may represent two or more superimposed frequencies, wherein one of the two or more sinusoidal signals is a harmonic of another sinusoidal signal.

BRIEF DESCRIPTION OF THE DRAWINGS

The foregoing and other features of the present disclosure will become more fully apparent from the following description and appended claims, taken in conjunction with the accompanied drawings. Understanding that these drawings depict only several embodiments in accordance with the disclosure and are not to be considered limiting of its scope, the disclosure will be described with additional specificity and detail through use of the accompanied drawings.

FIG. 13A shows a waveform of a sinusoidal signal, FIG. 13B shows a waveform of a PN code, and FIG. 13C shows a waveform of a modulated signal.

DETAILED DESCRIPTION OF EMBODIMENTS

Figure 1:
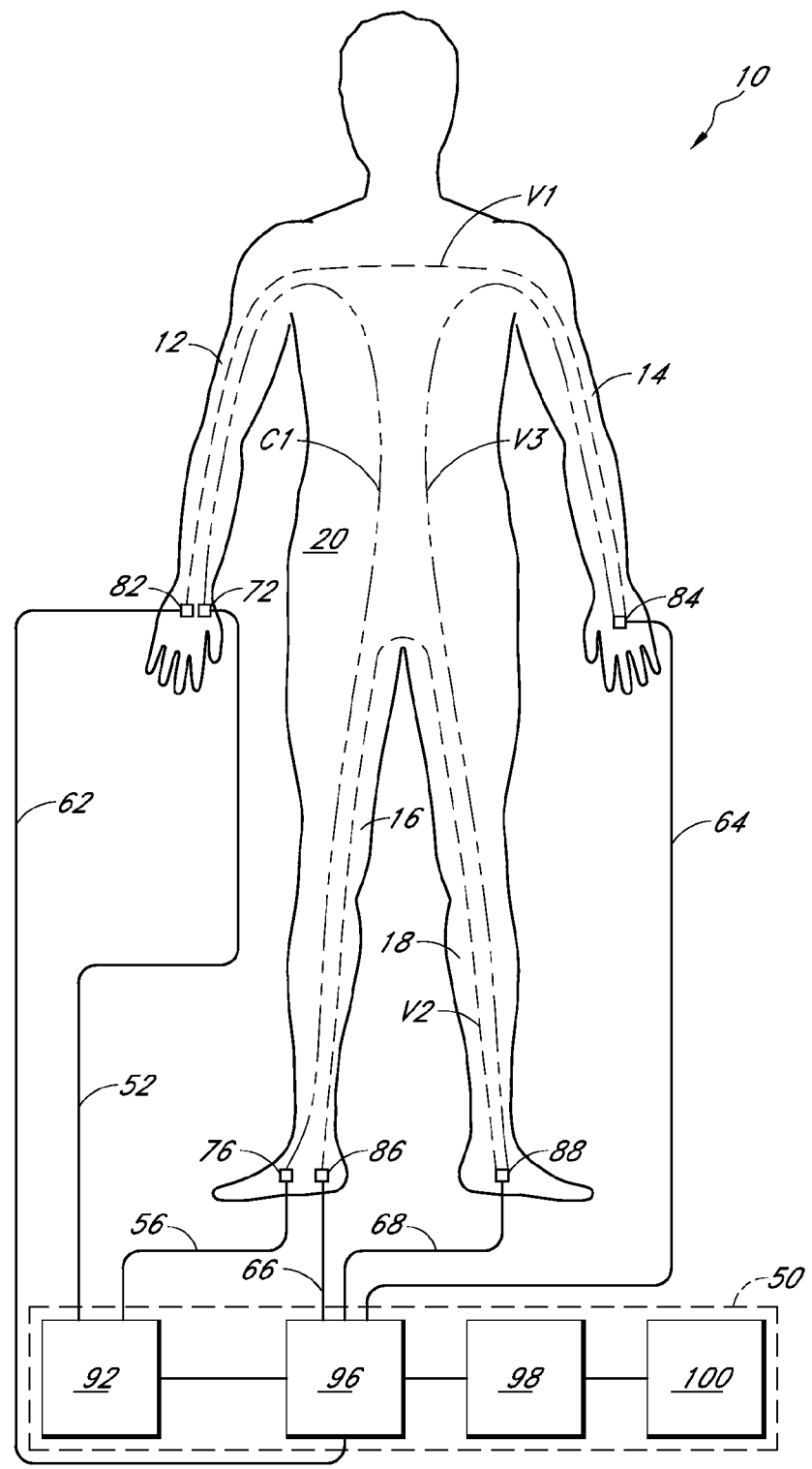
FIG. 1 is a schematic diagram depicting a connection configuration of a body composition analyzer and a human body for analyzing composition of the human body in accordance with one embodiment.

Embodiments will be described in detail hereinafter. In the following detailed description, reference is made to the accompanying drawings which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made without departing from the spirit or scope of the subject matter presented herein. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Throughout the disclosure, reference to "an embodiment" or "embodiments" means that a particular feature, structure, process, step, function, parameter, or characteristic described in connection with the embodiment(s) is included in at least one embodiment of the present invention. The phrases "in one embodiment" or "in embodiments" throughout this disclosure does not necessarily mean that the phrases all refer to the same embodiment(s). The particular feature, structure, process, step, function, parameter, or characteristic may be combined in any suitable manner in one or more embodiments.

Body Composition Analysis

A human body has a plurality of body segments, for example, arms, legs and trunk. In common use and in this disclosure, an arm refers to any part or parts of the entire upper extremity or limb including a hand and a wrist, and a leg refers to any part of parts of the entire lower extremity or limb including a foot and ankle.

In one embodiment, bioelectrical impedance analysis determines composition parameters, including an impedance value of each of the body segments. The impedance values can be processed to estimate the physiological condition of the subject's body or the amount of a body substance, for example, body water, which can be used to calculate fat-free mass. Further, the information on weight, body water and fat-free mass can be used for estimating body fat.

For the analysis of the body composition using impedance values, in one embodiment, at least a formula using impedance values of body segments can be provided. In another embodiment, a pre-established lookup table can be used for estimating body composition.

In one embodiment of the bioelectrical analysis, at least a current is applied through the subject's body and voltage levels are measured at several positions of the body. During the measurement, the movement of the subject's body during the measurement would affect the measured voltage levels and accuracy of body composition analysis. Thus, there is still a need to provide accurate analysis of body composition for a person, for example, a child or a patient that might move or change his physical position or posture during measurement. When time for acquiring data from the body is shortened, the physiological condition of the body can be analyzed or assessed more accurately. For this end, in one embodiment of the invention, voltage levels or signals from a plurality of positions of the body are simultaneously measured. In another embodiment, a plurality of currents or current signals are simultaneously applied or provided through the body. In some embodiments, a current signal can be a combined or mixed signal of multiple sinusoidal signals and represent multiple superimposed frequencies. The above embodiments will be discussed in detail in this specification.

Connection of Human Body and Body Composition Analyzer

Referring to FIG. 1, a human body 10 has a plurality of body segments including arms 12 and 14, legs 16 and 18, and a trunk 20. A body composition analyzer 50 is electrically connected to the body 10 via leads 52, 56, 62, 64, 66, 68 and electrodes 72, 76, 82, 84, 86, 88. In one embodiment, the analyzer 50 can include a current device or current source 92, and a voltage measuring device 96. The analyzer 50 can further include a processor 98 and a display 100.

With continuous reference to FIG. 1, in one embodiment, the current device 92 is connected to an electrode 72 attached to the right arm 12 and electrode 76 attached to the right leg 16 via leads 52, 56, respectively, to form a current flow path C1 passing through the right arm 12, the trunk 20 and the right leg 16. The term "connected to" is intended to have its ordinary meaning, including attached to, coupled to, touching, and/or in electrical communication with. "Connected" can refer to a physical or merely electrical link.

The voltage measuring device 96 is connected to an electrode 82 attached to the right arm 12 and electrode 86 attached to the right leg 16 via leads 62, 66, respectively. The voltage measuring device 96 is further connected to an electrode 84 attached to the left arm 14 and electrode 88 attached to the left leg 18 via leads 64, 68, respectively.

In the foregoing, the electrodes are attached to the body. Alternatively, the electrodes can touch the skin of the body without bonding to the body. In some embodiments, electric connection scheme of the body 10 and the analyzer 50 can be different from the foregoing embodiment, and various connection configurations will be discussed in detail later in this specification.

Position of Electrodes

Referring to FIG. 1, in one embodiment, the electrodes 72, 82 can be attached to different positions of the right hand 112 to be slightly spaced from each other. The electrode 82 is positioned near the electrode 72, but does not contact the electrode 72. The electrodes 76, 86 can be attached to different positions of the right foot 116 to be slightly spaced from each other. In the illustrated embodiment, each electrode is attached to the hand or foot. Alternatively, electrodes can be attached to the wrist or ankle. In some embodiments, electrodes are configured such that contacting electrodes with hands or feet provide electric connection between the body 10 and the analyzer 50. In other embodiments, the electrodes can be attached to the body by using adhesive.

Application of Current Signal

Referring to FIG. 1, in one embodiment, the current device 92 applies an electric current signal to the body 10 such that the current signal flows through the first current path C1. In one embodiment, the current signal can be applied for a time period. In one embodiment, the time period can be about 15 seconds to 5 minutes. In certain embodiments, the time period can be about 20 seconds, about 30 seconds, about 45 seconds, about 60 seconds, about 80 seconds, about 100 seconds, about 2 minutes, about 2.5 minutes, about 3 minutes, about 4 minutes, about 5 minutes, or about 6 minutes. In some embodiments, the time period can be a time interval within a range defined by two of the foregoing time intervals.

In one embodiment, the current signal represents a single sinusoidal signal with a single frequency. In another embodiment, the current signal is a combined signal of at least two sinusoidal signals to represent at least two superimposed frequencies. In certain embodiments, the current signal is a modulated signal from a sinusoidal signal in order to minimize an influence from an unwanted noise. These features will be further discussed below.

Measuring Voltage Signals

Referring to FIG. 1, the voltage measuring device 96 measures a voltage signal at each of the voltage measuring electrodes 82, 84, 86, 88. In one embodiment, the voltage signal measurement at the all electrodes 82, 84, 86, 88 can be performed simultaneously at least for a predetermined time period while the current signal is applied. The predetermined time period can be the same with or less than the time period of the application of the current signal. In this embodiment, since the measurement of the voltage signals are simultaneously performed, the time required for acquiring data from the person subject to the analysis can be shortened. Thus, analysis of physiological condition can provide more accurate results, as errors caused from the change of physical position or posture during measurement can be avoided. In one embodiment, only one time measurement can be sufficient to analyze or assess the body composition.

In some embodiments, a voltage signal is obtained at each of the measuring electrodes 82, 84, 86, 88 with respect to a predetermined reference voltage level. For example, in one embodiment, the predetermined reference voltage level is the ground level of the current device 92. In another embodiment, the predetermined reference voltage level is the voltage at one of the electrodes 82, 84, 86, 88. For example, in one embodiment, a voltage signal of each of electrodes 84, 86, 88 with reference to the voltage level of the electrode 82 can be acquired.

The obtained voltage signals are transmitted to the processor 98 for further processing. In certain embodiments, before transmitting, the voltage signals can be converted from analog signal to digital signal. In one embodiment, the processor 98 can have a memory for storing the voltage signals and circuitry for processing the obtained voltage signals.

Processing Measured Voltage Signals

In one embodiment, once the acquisition of voltage signals is completed, the processor 98 processes the obtained voltage signals so as to determine impedance value of each of the body segments 12, 14, 16, 18, 20. The process of determining the impedance value of each body segment will be discussed below.

Impedance Value of Right Arm

Referring to FIG. 1, in one embodiment, to determine the impedance value of the right arm 12, two measuring electrodes 82, 84 are selected. The processor 96 can retrieve voltage signals measured at the electrodes 82, 84. Subsequently, a voltage drop signal between the electrodes 82 and 84 is obtained by processing the voltage signals at the electrodes 82, 84, for example, by subtracting the voltage signal at the electrode 84 from the voltage signal at the electrode 82.

As schematically illustrated in FIG. 1, at the right arm 12, the current path C1 partially overlaps with a first voltage measuring path V1, which is a body path passing through two arms 12, 14 between two electrodes 82 and 84. As can be seen from FIG. 1, in one embodiment, the voltage drop signal between the electrodes 82 and 84 can be primarily or solely in response to the current signal passing through the right arm 12 since no current is delivered to the left arm 14. Generally, the voltage drop signal has the substantially same frequency with that of the current signal, but the voltage drop signal has a phase and an amplitude value different from those of the current signal, respectively.

In a certain embodiment, the impedance value of the right arm 12 can be calculated using the characteristics of the current signal and the voltage drop signal, for example, amplitude values of the signals. Where, the current signal and the voltage drop signal are defined as follows:

Current Signal=$c_1 \times \sin(n_1 wt)$; and

Voltage Drop Signal=$b_1 \times \sin(n_1 wt)$ the impedance value can be defined as follows:

$Z=b_1/c_1$

In another embodiment, the calculation of impedance value of the right arm 12 can be performed by processing the voltage drop signal and the current signal by using signal transformation process, for example, Fourier transform including FFT.

Impedance Value of Right Leg

With continued reference to FIG. 1, in one embodiment, to determine an impedance value of the right leg 16, two measuring electrodes 86, 88 are selected. The processor 96 can retrieve voltage signals measured at the electrodes 86, 88. Subsequently, a voltage drop signal between the electrodes 86 and 88 is obtained by processing the voltage signals at the electrodes 86, 88, for example, by subtracting the voltage signal at the electrode 88 from the voltage signal at the electrode 86.

As schematically illustrated in FIG. 1, at the right leg 16, the first current path C1 partially overlaps with a second voltage measuring path V2 which is a body path passing through two legs 16, 18 between two electrodes 86 and 88. In one embodiment, the voltage drop signal between the electrodes 86 and 88 can be primarily or solely in response to the current signal passing through the right leg 16 since no current is delivered to the left leg 18. Generally, the voltage drop signal has the substantially same frequency with that of the current signal, but the voltage drop signal has a phase and an amplitude value different from those of the current signal, respectively.

In one embodiment, in the same manner in determining the impedance value of the right arm 12, the impedance value of the right leg 16 can be determined from the voltage drop signal between the electrodes 86 and 88. From the voltage drop signal and the current signal, the impedance value of the right leg 16 can be determined.

Impedance Value of Trunk

Referring to FIG. 1, in one embodiment, to determine an impedance value of the trunk 20, two measuring electrodes 84, 88 are selected. The processor 96 can retrieve voltage signals measured at the electrodes 84, 88. Subsequently, a voltage drop signal between the electrodes 84 and 88 is obtained by processing the voltage signals at the electrodes 84, 88, for example, by subtracting the voltage signal at the electrode 88 from the voltage signal at the electrode 84.

As schematically illustrated in FIG. 1, at the trunk 20, the current path C1 partially overlaps a third voltage measuring path V3 which is a body path passing through the left arm 14, the trunk 20 and the left leg 18 between two electrodes 84 and 88. As can be seen from FIG. 1, in one embodiment, the voltage drop signal between the electrodes 84 and 88 can be primarily or solely in response to the current signal passing through the trunk 20 since no current is delivered to the left arm 14 or left leg 18. Generally, the voltage drop signal has the substantially same frequency with that of the current signal, but the voltage drop signal has the phase and the amplitude value different from those of the current signal, respectively.

In one embodiment, through the process used for determining impedance value of the right arm 12, the impedance value of the trunk 20 can be determined from the voltage drop signal between the electrodes 84 and 86. From the voltage drop signal and the current signal, the impedance value of the trunk 20 can be determined.

Impedance Value of Left Arm and Impedance Value of Left Leg

In one embodiment, the impedance value of the left arm 14 and the impedance value of the left leg 18 can be estimated from the impedance value of the right arm 12 and the impedance value of the right leg 16. In a certain embodiment, the impedance value of the left arm 14 can be estimated as the same value with that of the right arm 12, considering the right and left sides of the human body are generally symmetric. Likewise, the impedance value of the left leg 16 can be estimated as the same value with that of the right leg 18.

In one embodiment, the impedance values of the left arm and the left leg can be obtained by the way used for obtaining the impedance values of the right arm and the right leg as discussed above. In this embodiment, the electrodes 72 and 76 are detached from the right arm 12 and the right leg 16, and then, attached to the left arm 14 and the left leg 18. Subsequently, a current signal is applied from the current source 92, and then, voltage signals can be acquired at the electrodes 82, 84, 86, 88. From the obtained voltage signals, the impedance values of the left arm 14 and left leg 18 can be determined.

Analysis of Body Composition

In one embodiment, the impedance value of the body segments determined as above can be used to provide an estimate of a body component, for example, body water of the body, which can be used to estimate fat-free body mass. Further, the information on body water and fat-free mass can be used for estimation of body fat. In one embodiment, a formula using impedance values of body segments can provide estimation of body composition. Various formulas can be used for estimating the body composition.

In one embodiment, the impedance values can be used to estimate the amount of body water, which can be used to calculate fat-free mass. Further, using weight, body water and fat-free mass, body fat can be estimated. In one non-limiting embodiment, the total body water (TBW) is the sum of the segmental water, and can be defined as follows:

$$TBW = C_1(Ht^2/Z_{ra} + Ht^2/Z_{la}) + C_2 Ht^2/Z_t + C_3(Ht^2/Z_{rl} + Ht^2/Z_{ll})$$

wherein $C_1$, $C_2$, $C_3$ are constants derived from experimental data and/or a model, and Ht is the height of the measuring person. $Z_{ra}$, $Z_{la}$, $Z_t$, $Z_{rl}$, $Z_{ll}$ are the impedance values of the right arm 12, the left arm 14, the trunk 20, the right leg 16, the left leg 18. As shown, total body water can be obtained from the impedance values and the height.

Body fat would contain relatively small amount of water, and thus this water content can be disregarded in one embodiment. In certain embodiments, total body water can be regarded as about 73% of the fat free mass (FFM), and therefore, FFM is defined as follow:

$$FFM = TBW/0.73$$

In some embodiments, the amount of body fat (FAT) can be defined as subtraction of FFM from the whole body weight (Wt), thus body fat (FAT) and body fat percentage (% BF) can be defined as follows:

$$FAT = Wt - FFM$$

$$\% BF = 100(Wt - FFM)/Wt$$

Formulas described in U.S. Pat. No. 6,256,532 can further be used for analyzing of body composition of whole body or body segments, and the disclosure of U.S. Pat. No. 6,256,532 is incorporated herein by reference in its entirety.

Display of Body Composition

In one embodiment, the data of the body composition is displayed in the display 100. In another embodiment, the data of the body composition can be printed out.

Impedance

In the foregoing embodiments, impedance values of body segments are determined and used for analyzing body composition or a physiological condition. In certain embodiments, instead of impedance, another kind of parameter of body segments can be obtained during a signal transformation process and used to analyze or assess body composition. In one embodiment, the other parameter of each body segment has a value substantially proportional to the impedance value of each segment. In other embodiments, the value of the other parameter of each segment is not proportional with the impedance value of each segment. In this specification, a term "composition parameter" is used to represent impedance and such a parameter discussed above.

Another Configuration of Connecting Body and Analyzer

Figure 2:
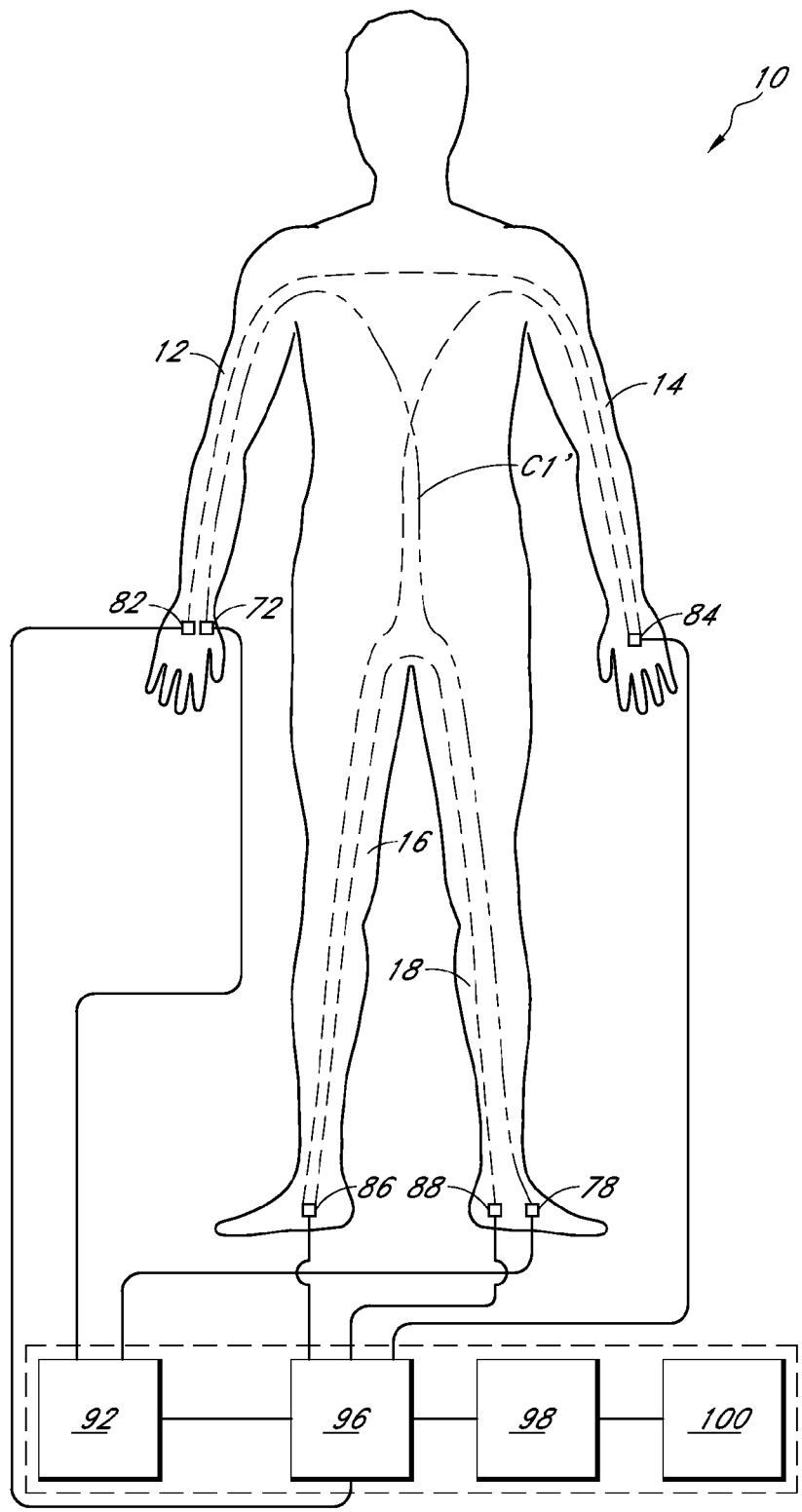
FIG. 2 illustrates a schematic diagram including a connection configuration of a body composition analyzer and a human body for analyzing composition of the human body in accordance with one embodiment.

Referring to FIG. 2, in one embodiment, the current device 92 applies a current signal to the body 10 such that a current signal C1' flows through a first current path passing through the right arm 12, the trunk 20 and the left leg 18 between electrodes 72 and 78. The voltage measuring device 96 measures a voltage signal at each of the voltage measuring electrodes 82, 84, 86, 88. The voltage signal measurement at the all electrodes 82, 84, 86, 88 can be performed simultaneously for a time period while the current signal is applied.

In this configuration, impedance value of the right arm 12 can be obtained in the same manner used in the configuration shown in FIG. 1. That is, the impedance value of the right arm 12 can be determined using the voltage drop signal between the electrodes 82 and 84 with reference to the current signal. The impedance value of the left leg 18 can be determined using the voltage drop signal between the electrodes 86 and 88 with reference to the current signal. The impedance value of the trunk 20 can be determined using the voltage drop signal between the electrodes 84 and 86 with reference to the current signal.

In one embodiment, the impedance values of the left arm 14 and the right leg 16 can be determined in the same way with the process used in the configuration discussed above. Further, the body composition can be assessed in the same manner used in the configuration discussed above and shown in FIG. 1.

Current Path and Voltage Signal Measuring

The following table shows various current paths and voltage pickup positions for measuring an impedance of each body segment.

TABLE 1

Current paths and voltage pickup positions for of each body segment

| Body Segment | Current Path | Voltage Pickup Positions |
|---|---|---|
| RA | RA-RL | Between RA and LA |
|  | RA-LL | Between RA and LA |
|  | RA-LA | Between RA and RL, or between RA and LL |
| LA | LA-RL | Between LA and RA |
|  | LA-LL | Between LA and RA |
|  | LA-RA | Between LA and LL, or between LA and RL |
| RL | RL-RA | Between RL and LL |
|  | RL-LA | Between RL and LL |
|  | RL-LL | Between RL and RA, or between RL and LA |
| LA | LL-RA | Between LL and RL |
|  | LL-LA | Between LL and RL |
|  | LL-RL | Between LL and LA, or between LL and RA |
| Trunk | RA-RL | Between LA and LL |
|  | RA-LL | Between LA and RL |
|  | LA-LL | Between RA and RL |
|  | LA-RL | Between RA and LL |

(RA: right arm, LA: left arm, RL: right leg, LL: left leg)

Yet Another Configuration of Connecting Body and Analyzer

Figure 3:
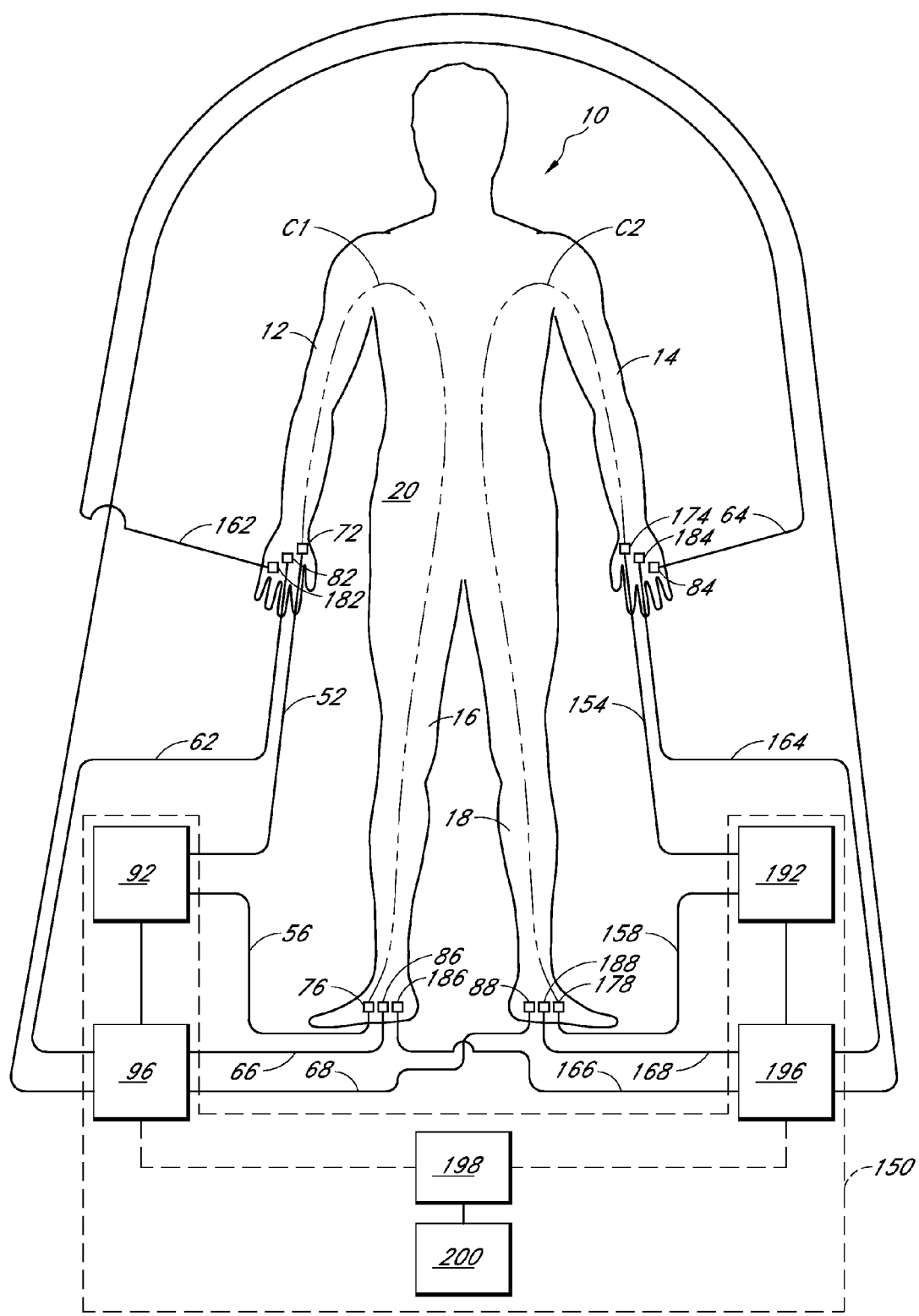
FIG. 3 shows a schematic diagram of a connection configuration of a human body and a body composition analyzer in accordance with one embodiment.

Referring to FIG. 3, in one embodiment, a body composition analyzer 150 has a first current device 92, a second current device 192, a first voltage measuring device 96 and a second voltage measuring device 196. The analyzer 150 further has a processor 198 and a display 200. In some embodiments, the processor 198 can receive voltage signals from the voltage measuring devices 96, 196 using wired communication or wireless communication. The processor 198 can receive voltage signals from the voltage measuring devices 96, 196 using electric signal transmission or nonelectric signal transmission.

In one embodiment, the current device 92 is connected to an electrode 72 attached to the right arm 12 and electrode 76 attached to the right leg 16 via leads 52, 56, respectively, to form a current flow path C1 passing through the right arm 12, the trunk 20 and the right leg 16. The second current device 192 is connected to an electrode 174 attached to the left arm 14 and electrode 178 attached to the left leg 18 via leads 154, 158, respectively, to form a current flow path C2 passing through the left arm 14, the trunk 20 and the left leg 18.

The voltage measuring device 96 is connected to an electrode 82 attached to the right arm 12 and electrode 86 attached to the right leg 16 via leads 62, 66, respectively. The voltage measuring device 96 is further connected to an electrode 84 attached to the left arm 14 and electrode 88 attached to the left leg 18 via leads 64, 68, respectively. Similarly, the voltage measuring device 196 is connected to an electrode 182 attached to the right arm 12 and electrode 186 attached to the right leg 16 via leads 162, 166, respectively. The voltage measuring device 196 is further connected to an electrode 184 attached to the left arm 14 and electrode 188 attached to the left leg 18 via leads 164, 168, respectively.

Electrical Decoupled Current Devices

Figure 4:
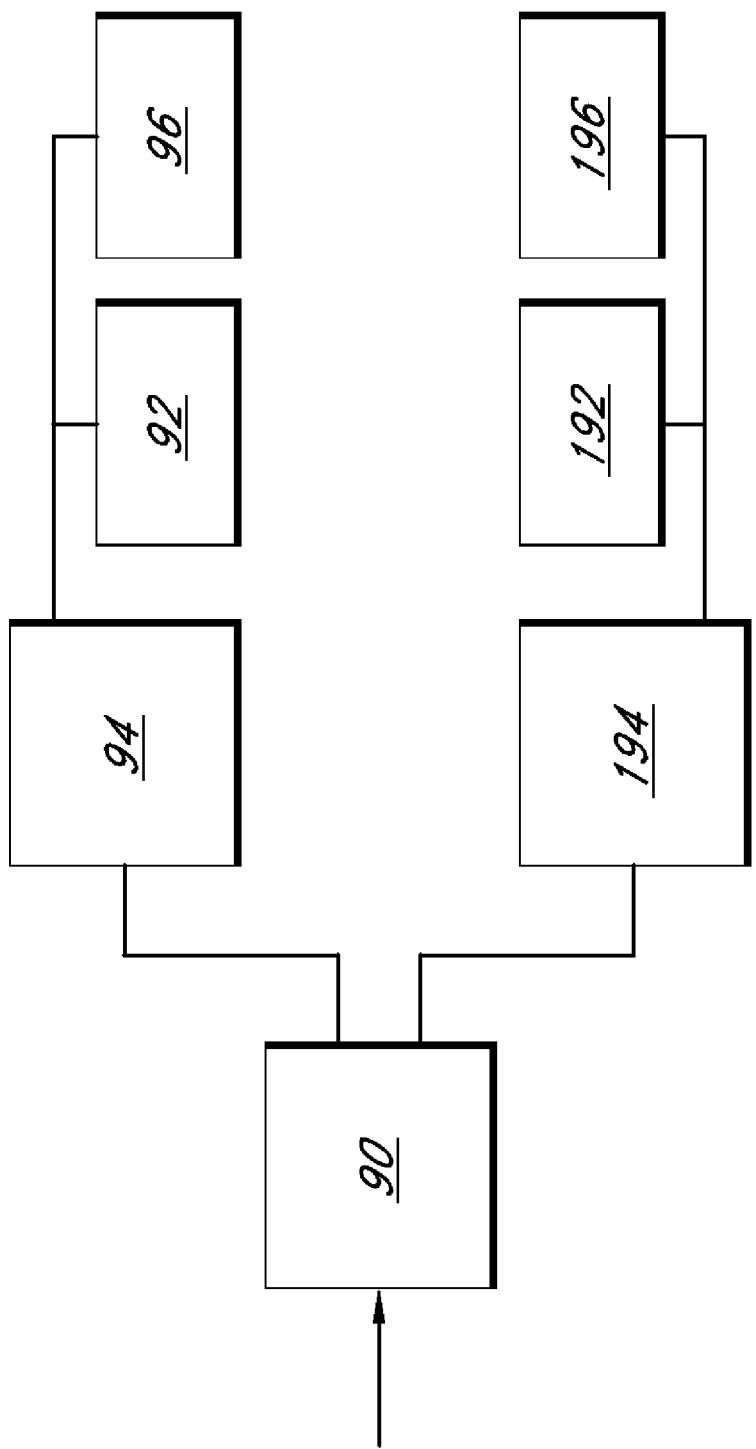
FIG. 4 is a block diagram showing relationship between two current sources shown in FIG. 3.

Referring to FIGS. 3 and 4, in some embodiments, the first current device 92 is electrically decoupled from the second current device 192. In particular, a circuit or a ground of the first current device 92 is electrically decoupled from or decoupled from a circuit or a ground of the second current device 192. An example of this configuration is shown in FIG. 4.

Referring to FIG. 4, the alternating current electric power is supplied to the first current device 92 and the second current device 192 from a distributer 90. Between the distributer 90 and the first current device 92, an isolator, for example, a first transformer 94, is provided. Likewise, between the distributer 90 and the second current device 192, a second transformer 194 is provided. In this configuration, the current devices 92 and 192 are electrically decoupled from each other as the electric power is supplied via the transformers 94 and 194. The first and second voltage measuring devices 96 and 196 are connected to the first and second current devices 92 and 192, respectively, and are decoupled from each other.

Measurement of Voltage Signals

Figure 5:
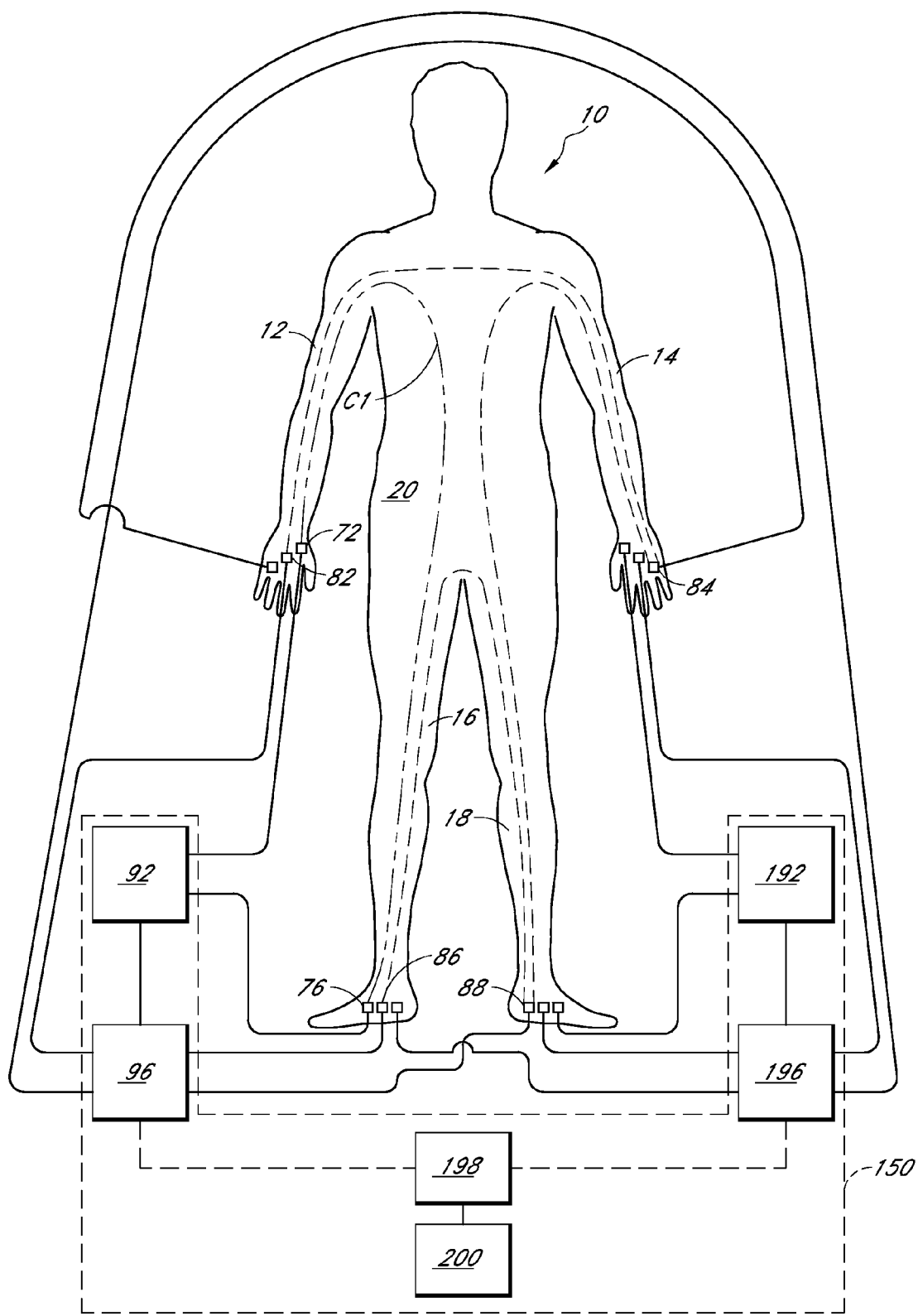
FIGS. 5 and 6 are schematic diagrams showing voltage measuring processes in the connection configuration shown in FIG. 3.

As shown in FIG. 5, the voltage measuring device 96 measures a first group of voltage signals at the voltage measuring electrodes 82, 84, 86, 88. The voltage signal measurement at the all electrodes 82, 84, 86, 88 can be performed simultaneously for a time period while the first and second current signals are simultaneously applied. In a certain embodiment, a voltage signal at each of the measuring electrodes 82, 84, 86, 88 can be obtained relative to a ground level of the first circuit device 92. The obtained voltage signals can be transmitted to the processor for further processing with or without conversion to digital signal.

Figure 6:
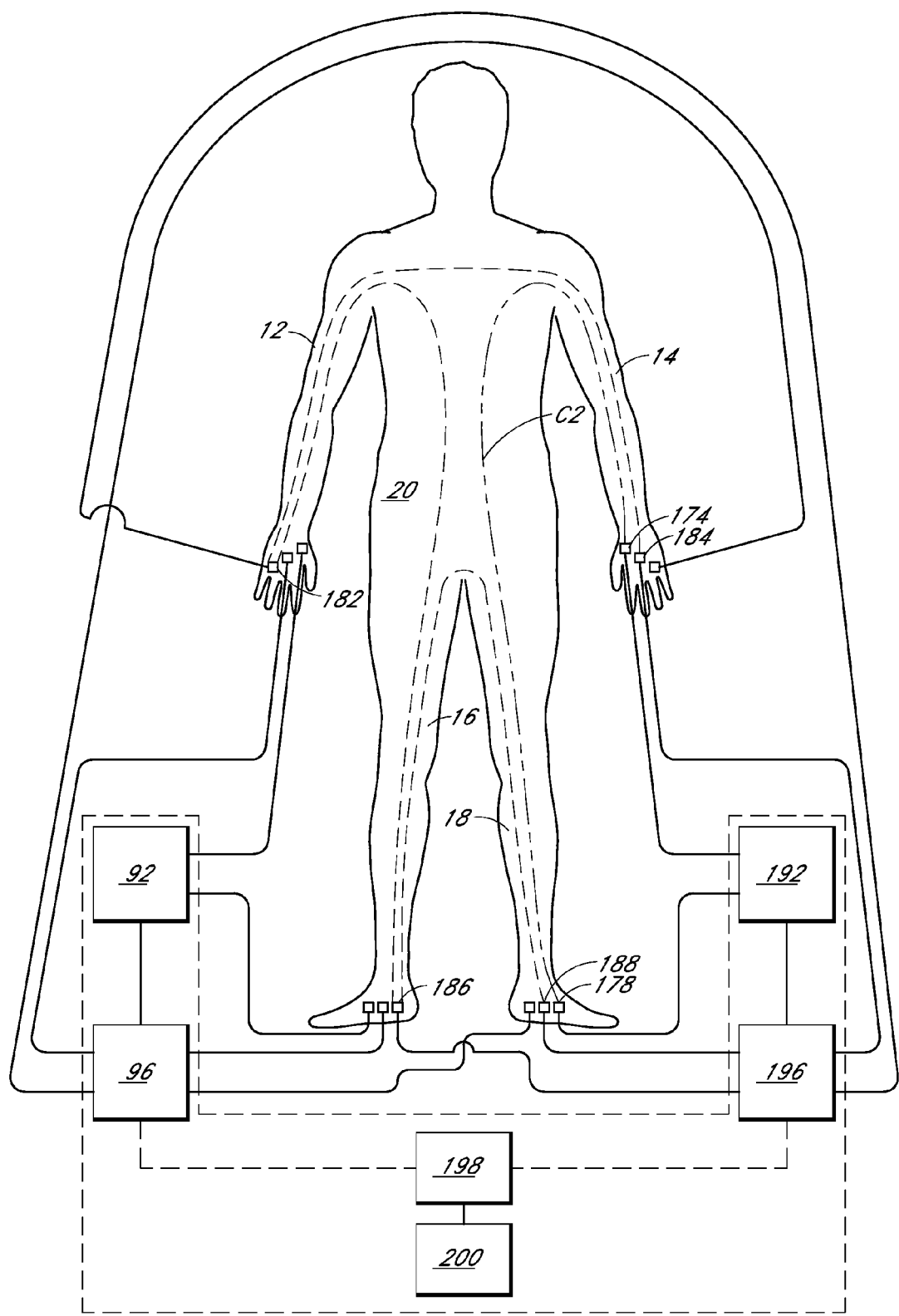

Likewise, as shown in FIG. 6, the voltage measuring device 196 measures a second group of voltage signals at each of the voltage measuring electrodes 182, 184, 186, 188. The voltage signal measurement at the all electrodes 182, 184, 186, 188 can be performed simultaneously for a time period while the first and second modulated current signals are simultaneously applied. In a certain embodiment, a voltage signal at each of the measuring electrodes 182, 184, 186, 188 can be obtained relative to a ground level of the second current device 192. The measured voltage signals can be transmitted to the processor for further processing with or without conversion to digital signal. In certain embodiments, the measurement of the first group of voltage signals can be performed simultaneously with the measurement of the second group of voltage signals.

In the illustrated embodiment, since the application of multiple current signals and the measurement of the voltage signals are simultaneously performed, the time required for acquiring data from the person subject to the body composition analysis can be shortened. Thus, analysis of physiological condition can provide more accurate results, as errors caused from the change of physical position or posture during measurement can be avoided. In one embodiment, only one time measurement can be sufficient to assess or analyze the body composition.

Determining of Impedance and Analysis of Body Composition

Referring to FIG. 5, in one embodiment, the impedance value of the right arm 12 can be determined using the first current signal and two voltage signals measured from the electrode 82, 84 among the first group of the voltage signals. Likewise, the impedance value of the right leg 16 can be determined using two voltage signals measured from the electrode 86, 88 among the first group of the voltage signals. The impedance value of the trunk 20 can be determined using two voltage signals measured from the electrode 84, 88 among the first group of the voltage signals.

Referring to FIG. 6, the impedance value of the left arm 14 can be determined using the second current signal and two voltage signals measured from the electrode 182, 184 among the second group of the voltage signals. Likewise, the impedance value of the left leg 18 can be determined using two voltage signals measured from the electrode 186, 188 among the second group of the voltage signals. The impedance value of the trunk 20 can be further determined using two voltage signals measured from the electrode 82, 86 among the second group of the voltage signals.

From the determined impedance values of the body segments, body composition can be assessed in the same manner discussed above.

Frequency Difference of the First and Second Current Signal

Generally, the cell membrane penetration characteristic of a high frequency current signal can be different from that of the low frequency current signal. The high frequency current signal tends to penetrate the cell membrane more effectively than the low frequency current signal. A human body has water, which includes intracellular water and extracellular water. This allows the high frequency signal to pass through both intracellular and extracellular water, while the low frequency signal passes through extracellular water. Thus, in a human body, conduction of the high frequency current signal can be different from that of the low frequency current signal.

Accordingly, a measured impedance value of a body segment can vary in accordance with the frequency of the applied current signal. Various impedance values of body segments with respect to various frequencies can provide accurate analysis of body water, and further provide accurate analysis of body content.

In one embodiment, the application of mixed current signals and the analysis process of the mixed voltage signal are provided. Such configuration can make the time required for acquiring data from the person subject to the body composition analysis to be shortened. Thus, analysis of physiological condition can provide more accurate results, as errors caused from the change of physical position or posture during measurement can be avoided. In one embodiment, only one time measurement can be sufficient to assess or analyze the body composition.

For the configuration illustrated in FIGS. 3-6, in one embodiment, the first current signal passing through the first path C1 has a first frequency and the second current signal passing through the second path C2 has a second frequency, and the second frequency can be different from the first frequency. In certain embodiments, the first frequency can be smaller than about 50 KHz, while the second frequency can be greater than about 200 KHz, but not limited thereto. In some embodiments, the first frequency can be one of about 1 KHz, about 5 KHz, and about 50 KHz, and the second frequency can be one of about 250 KHz, about 500 KHz, and about 1 MHz.

In one embodiment, the first and second current signals having different frequencies can be simultaneously applied.

While the first and second current signals are simultaneously applied, the first group of voltage signals and the second group of voltage signals can be simultaneously measured in the same manner disclosed above. In this embodiment, the first group of voltage signals is responsive to the first frequency and the second group of voltage signals is responsive to the second frequency.

As shown in FIG. 6, the impedance values of the right arm 12, trunk 20 and right leg 16 with respect to the first frequency can be determined using the first group of voltage signals responsive the first frequency in the same manner discussed above. The impedance values of the left arm 14 and the left leg 18 with respect to the first frequency can be estimated from the impedance values of the right arm 12 and right leg 16. Alternatively, the impedance values of the left arm 14 and the left leg 18 with respect to the first frequency can be obtained through additional measurement.

The impedance values of the left arm 14, trunk 20 and left leg 18 with respect to the second frequency can be determined using the second group of voltage signals responsive to the second frequency in the same manner discussed above. The impedance values of the right arm 12 and the right leg 16 with respect to the second frequency can be estimated from the impedance values of the left arm 14 and left leg 16 with respect to the second frequency. Alternatively, the impedance values of the left arm 14 and the left leg 18 with respect to the second frequency can be obtained through additional measurement.

Body composition can be assessed or analyzed using impedance values of the body segments with respect to each of the first frequency and the second frequency. In one embodiment, total body water can be calculated using the impedance values. The equations and coefficients for the above calculation can vary. In a non-limiting embodiment, an equation can be as follows:

$$TBW = C_1(Ht^2/(a_1 Z_{ra1} + a_2 Z_{ra2}) + Ht^2/(a_1 Z_{la1} + a_2 Z_{la2})) + C_2 Ht^2/(t_1 Z_{t1} + t_2 Z_{t2}) Z_t + C_3(Ht^2/(l_1 Z_{rl1} + l_2 Z_{rl2}) + Ht^2/(l_1 Z_{ll1} + l_2 Z_{ll2}))$$

wherein $C_1, C_2, C_3, a_1, a_2, t_1, t_2, l_1, l_2$, are constants derived from experimental data and/or a model, and Ht is the height of the measuring person. $Z_{ra1}, Z_{la1}, Z_{t1}, Z_{rl1}, Z_{ll1}$ are impedance values of the right arm 12, the left arm 14, the trunk 20, the right leg 16, the left leg 18 with respect to the first frequency. $Z_{ra2}, Z_{la2}, Z_{t2}, Z_{rl2}, Z_{ll2}$ are impedance values of the right arm 12, the left arm 14, the trunk 20, the right leg 16, the left leg 18 with respect to the second frequency. Body composition can be further assessed or analyzed using the determined total body water in the same manner discussed above.

A Further Configuration of Connecting Body and Analyzer

Figure 7:
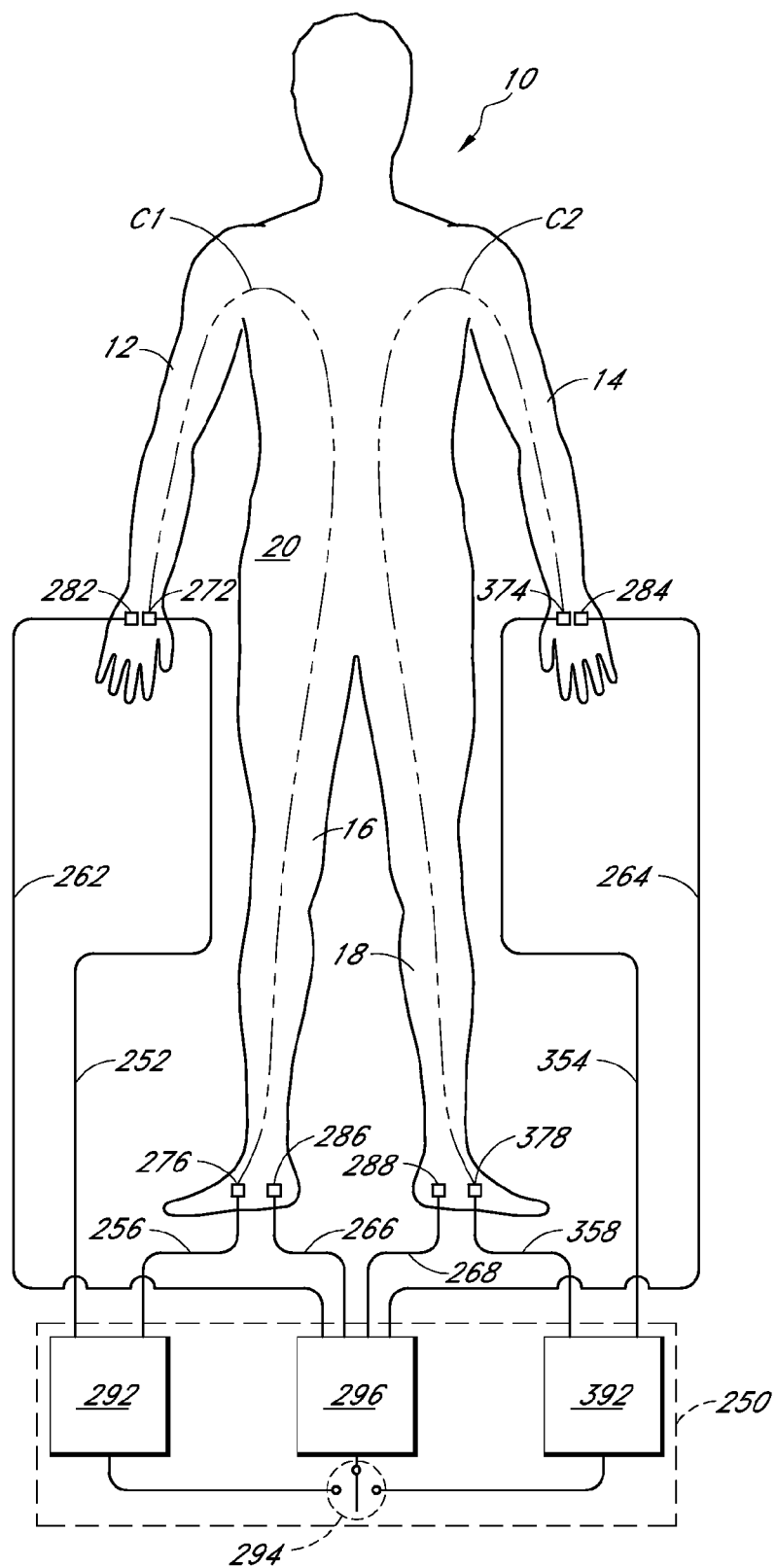
FIG. 7 shows a schematic diagram of a connection configuration of a human body and a body composition analyzer in accordance with one embodiment.

Referring to FIG. 7, in one embodiment, a body composition analyzer 250 has a first current device 292, a second current device 392, and a voltage measuring device 296. The analyzer further has a switch 294 for switching the connection of the voltage measuring device 296 between the first current device 292 and the second current device 392.

In one embodiment, the current device 292 is connected to an electrode 272 attached to the right arm 12 and electrode 276 attached to the right leg 16 via leads 252, 256, respectively, to form a current flow path C1 passing through the right arm 12, the trunk 20 and the right leg 16. The second current device 392 is connected to an electrode 374 attached to the left arm 14 and electrode 378 attached to the left leg 18 via leads 354, 358, respectively, to form a current flow path C2 passing through the left arm 14, the trunk 20 and the left leg 18. In some embodiments, the first current signal and the second current signal can be simultaneously applied to the body for a predetermined time period.

Figure 8:
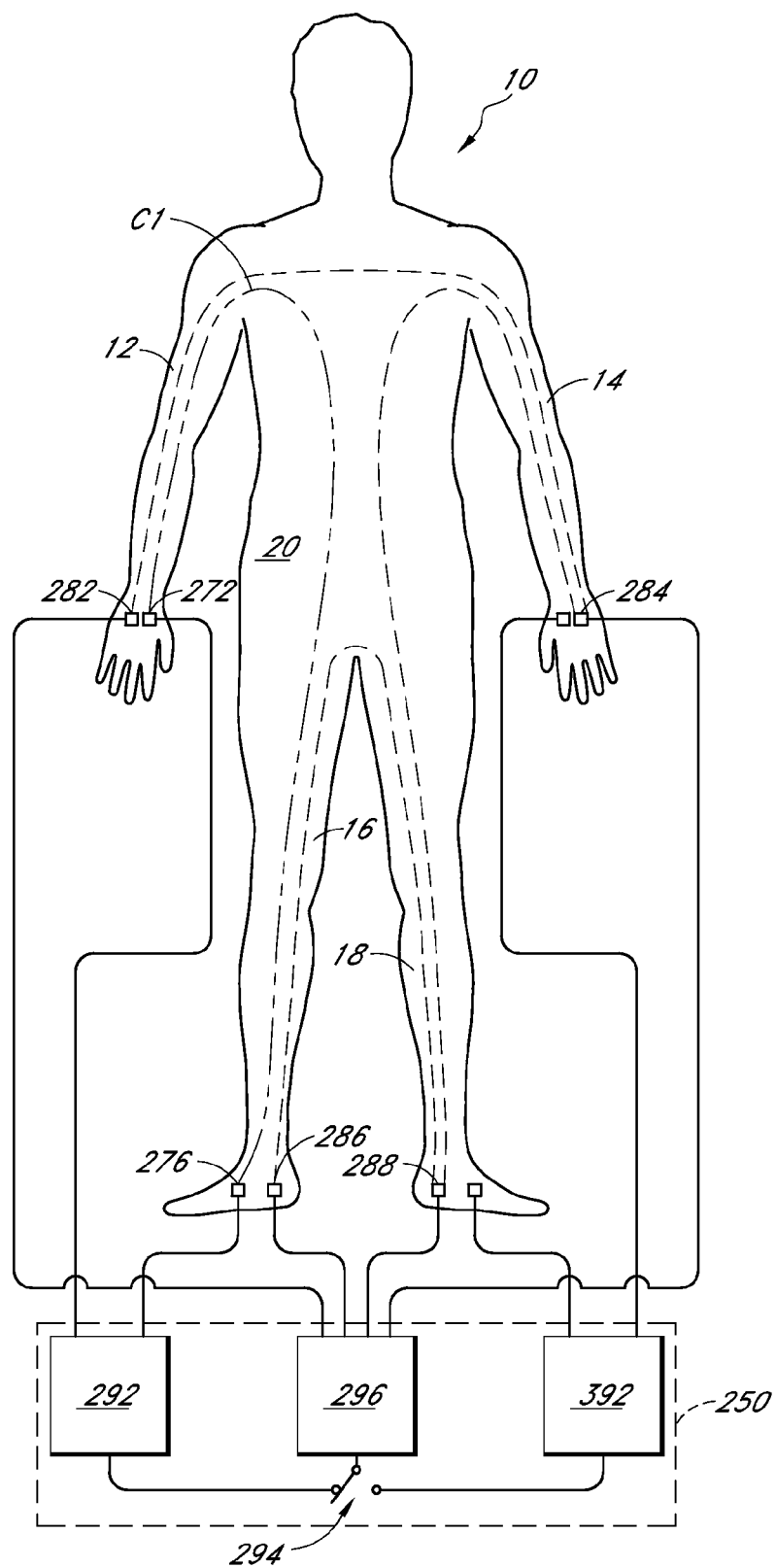
FIGS. 8 and 9 are schematic diagrams showing voltage measuring processes in the connection configuration shown in FIG. 7.
Figure 9:
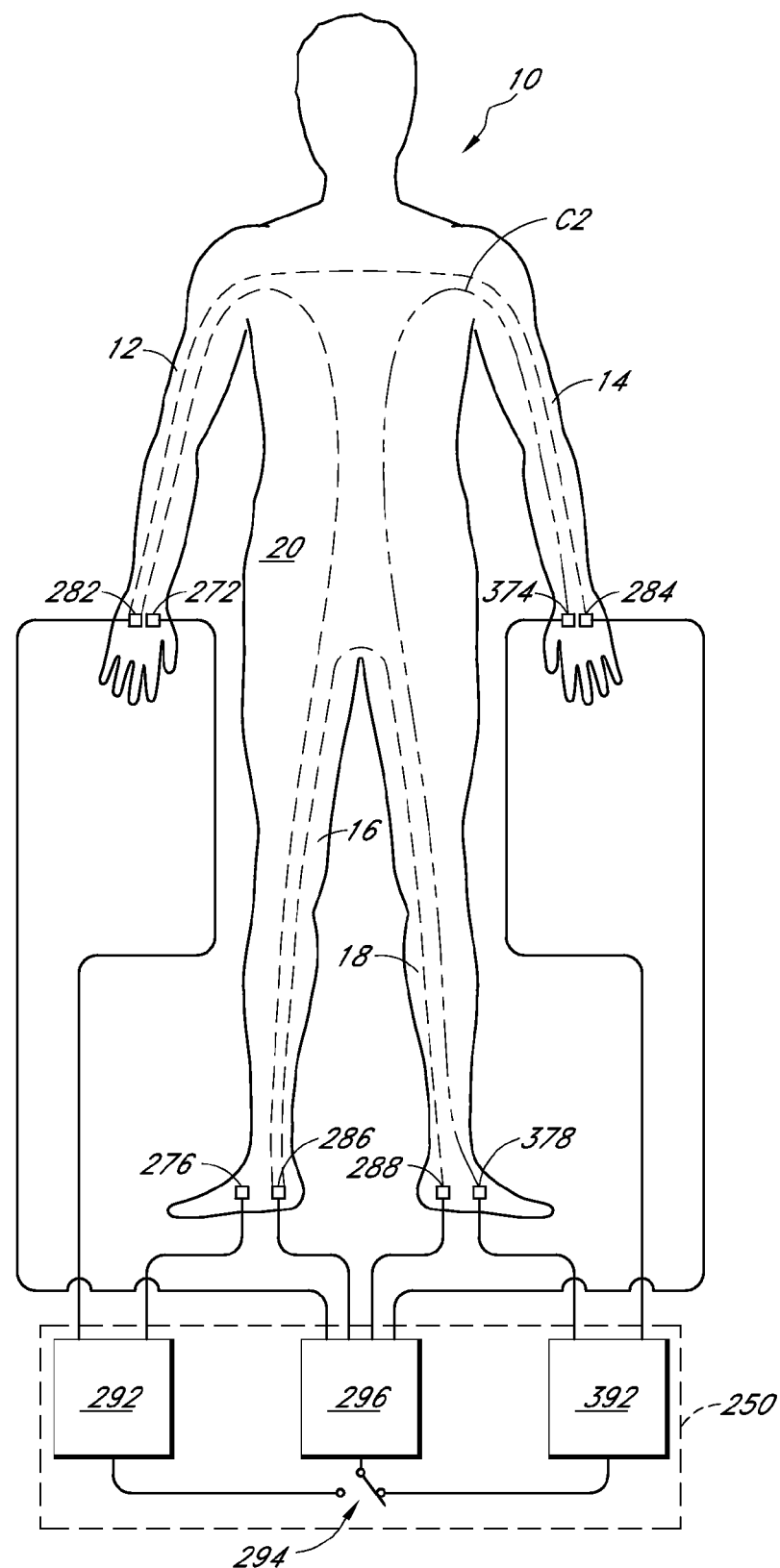

Referring to FIGS. 7-9, in some embodiments, the first current device 292 is electrically decoupled from the second current device 392. In particular, a circuit or a ground of the first current device 292 is electrically decoupled from a circuit or a ground of the second current device 392, for example, in the manner described above and illustrated FIG. 4.

The voltage measuring device 296 is connected to an electrode 282 attached to the right arm 12 and electrode 286 attached to the right leg 16 via leads 262, 266, respectively. The voltage measuring device 296 is further connected to an electrode 284 attached to the left arm 14 and electrode 288 attached to the left leg 18 via leads 264, 268, respectively.

As shown in FIG. 8, when the switch 294 maintains the electric connection between the voltage measuring device 296 and the first current device 292, the voltage measuring device 296 measures a first group of voltage signals at the voltage measuring electrodes 282, 284, 286, 288. The voltage signal measurement at the all electrodes 282, 284, 286, 288 can be performed simultaneously for a time period while the first current signal is applied. In a certain embodiment, a voltage signal at each of the measuring electrodes 282, 284, 286, 288 can be obtained relative to a ground level of the first circuit device 292. The obtained voltage signals can be transmitted to the processor for further processing with or without conversion to digital signal.

Likewise, as shown in FIG. 9, when the switch 294 maintains the electric connection between the voltage measuring device 296 and the first current device 392, the voltage measuring device 296 measures a second group of voltage signals at each of the voltage measuring electrodes 282, 284, 286, 288. The voltage signal measurement at the all electrodes 282, 284, 286, 288 can be performed simultaneously for a time period while the second modulated current signal is applied. In a certain embodiment, a voltage signal at each of the measuring electrodes 282, 284, 286, 288 can be obtained relative to a ground level of the second current device 392. The measured voltage signals can be transmitted to the processor for further processing with or without conversion to digital signal.

In this configuration, the impedance values of the body segments 12, 14, 16, 18, 20 can be determined, and the body composition can be assessed or analyzed using the determined impedance values in the same manner discussed above.

Mixed Current Signal of Multiple Frequencies

In some embodiments, a current signal can be a mixed current signal that represents at least two superimposed frequencies. For example, the current devices 92, 192, 292, 392 can have a configuration of any one of the current devices 500, 600, 700 shown in FIGS. 10, 11 and 12. In each of the illustrated embodiments, the current signal is applied between the right arm and right leg, and the voltage drop signal is measured between the left arm and left leg for measuring impedance values of the trunk, but not limited thereto. In other embodiments, the current application path and voltage measuring positions can vary as described in Table 1.

Figure 10:
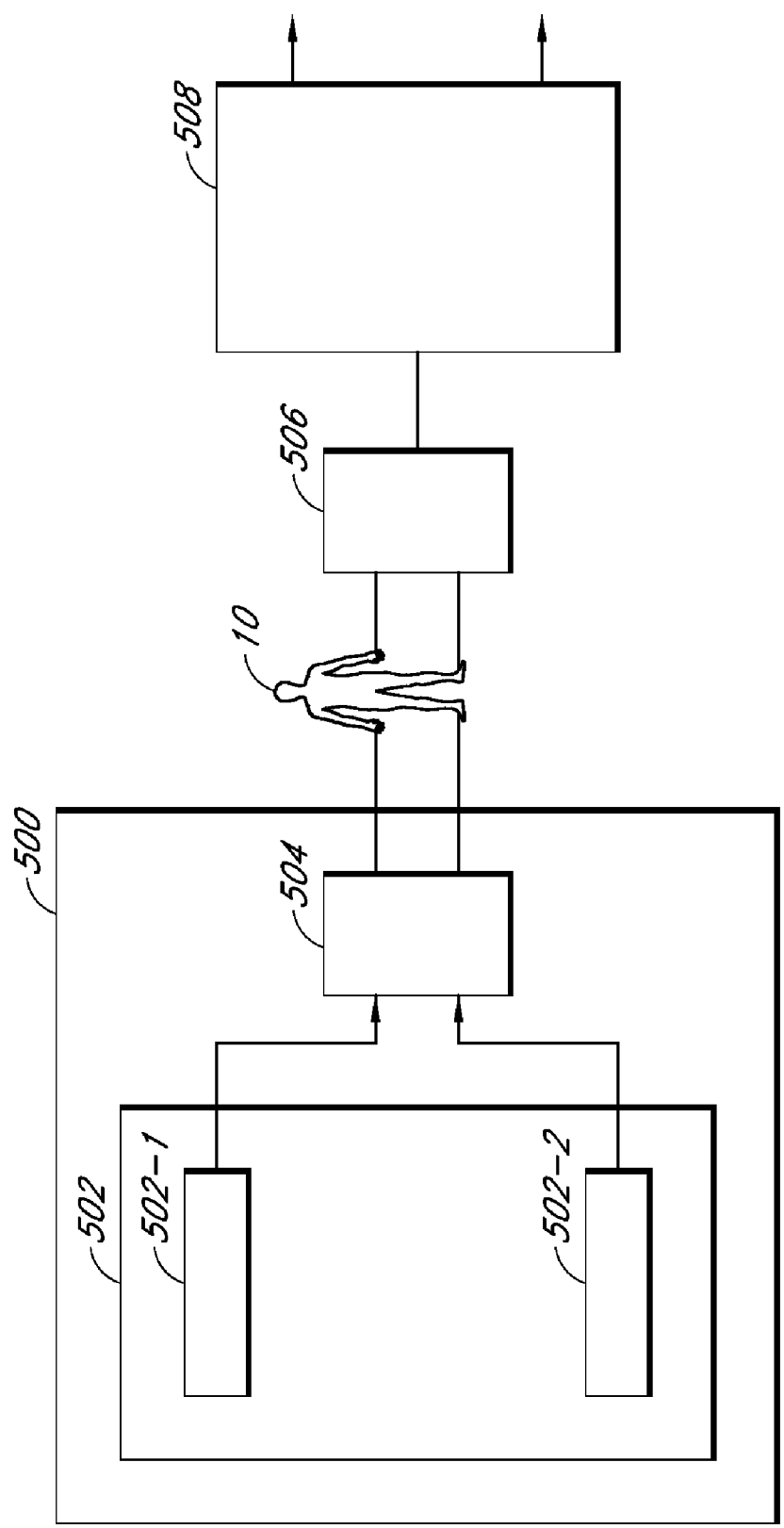
FIG. 10 depicts a block diagram of a body composition analyzer using a mixed signal of multiple frequencies in accordance with one embodiment.

Referring to FIG. 10, in one embodiment, the current device 500 has a plurality of sinusoidal current signal generators 502-1, 502-2. The FIG. 10 shows that the current device 500 has two signal generators and applies a current signal representing two frequencies, but not limited thereto. In other embodiments, the current signal can represent 3, 4, 5, 6 or more superimposed frequencies. In one embodiment, the signal generator 502 generates two sinusoidal current signals having different frequencies.

The sinusoidal current signals can be expressed, for example, $a_1 \cdot \sin(n_1 wt)$, $a_2 \cdot \sin(n_2 wt)$. In one embodiment, one signal is a harmonic of the other signal. In a certain embodiment, each of the frequencies of the current sinusoidal signals can be one selected from about 1 KHz, about 5 KHz, about 10 KHz, about 50 KHz, about 100 KHz, about 250 KHz, about 500 KHz, about 1 MHz. The generated sinusoidal signals can be combined in a combiner or adder 504, and then the combined signal is applied to the body 10 in the same manner discussed above.

A voltage drop signal between two points of the body 10 is measured by a voltage measuring device 506. Generally, the measured voltage drop signal can be a combined signal of two sinusoidal voltage signals, each of which has the same frequency with that of each sinusoidal current signal of the combined current signal, but has an amplitude value and a phase different from those of each sinusoidal current signal of the combined current signal.

To determine impedance with respect to each frequency of a body segment, the combined current signal and the voltage drop signal can be processed in a processor 508. In one embodiment, in the processor 508, the voltage drop signal can be assessed or analyzed using signal transformation process, for example, Fourier transform including FFT. For this, the processor 508 can include a FFT analyzer. Through the FFT of the voltage drop signal, values to be used to compute the impedance for each frequency can be obtained.

Alternatively, in another embodiment, a sinusoidal signal included in the voltage drop signal for each frequency can be separated by way of filtering the voltage drop signal. For this, the processor 508 can have a filter for each frequency. After filtering the voltage drop signal into two sinusoidal voltage signals, the impedance values for the frequencies can be obtained using characteristics of the sinusoidal voltage signals and the sinusoidal current signals.

Figure 11:
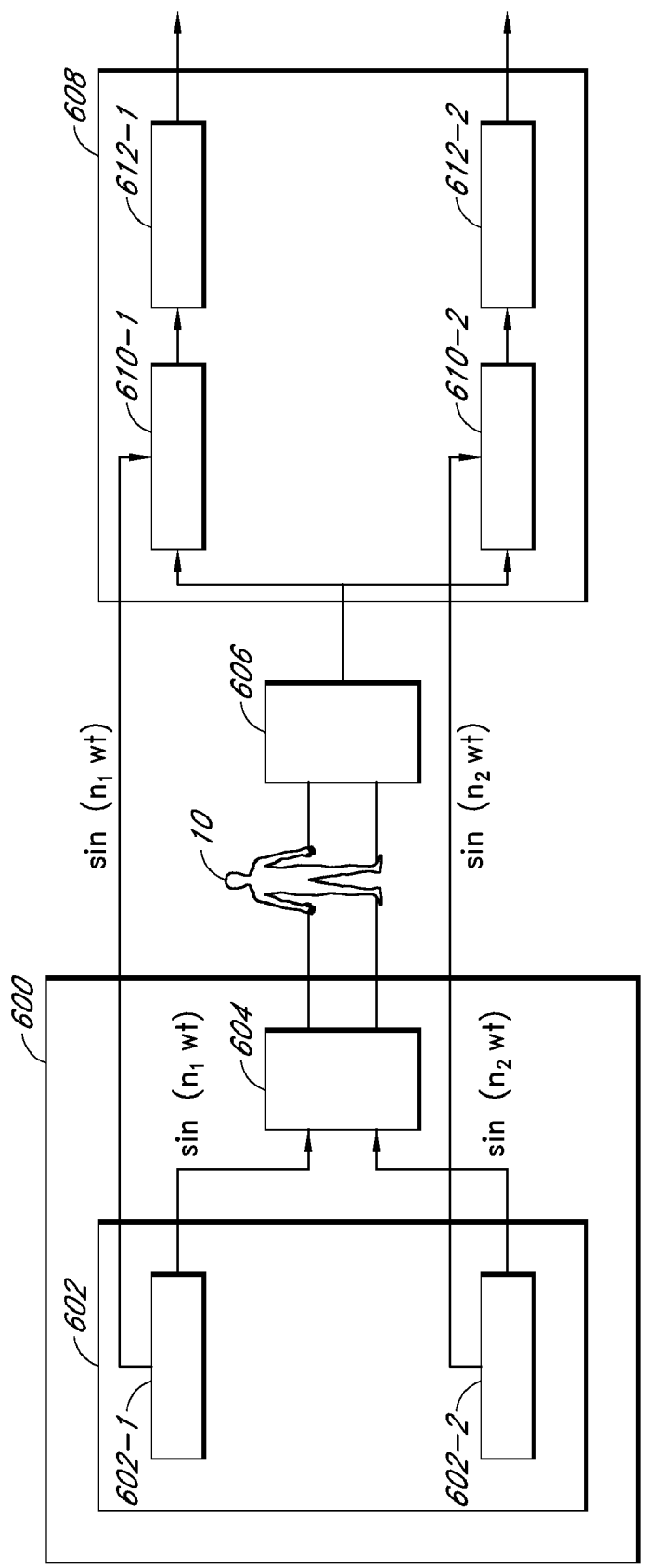
FIG. 11 is a block diagram of a body composition analyzer using a mixed signal of multiple frequencies in accordance with another embodiment.

In other embodiments, an impedance value for each frequency can be obtained by using other processes. FIG. 11 depicts one embodiment, which will be described in one of the other processes in detail below.

Processing of Mixed Voltage Signal of Multiple Frequencies

In one embodiment, as shown in FIG. 11, a current device 600 can have a same configuration with that shown in FIG. 10. Sinusoidal current signal generators 602-1, 602-2 generate sinusoidal signals having different frequencies. In a certain embodiment, the sinusoidal current signals can be expressed as, for example, a first sinusoidal current signal $\sin(n_1 wt)$ having a first frequency $f_1$ and a first period $T_1$, and a second sinusoidal current signal $\sin(n_2 wt)$ having a second frequency $f_2$ and a second period $T_2$. The second sinusoidal current signal is a harmonic of the first sinusoidal current signal. The generated sinusoidal signals can be mixed or combined in an adder 604, and then the mixed or combined signal is applied to the body 10 and a voltage drop signal can be measured in the same manner discussed above.

The voltage drop signal between two points of the body 10 is measured by a voltage measuring device 606. In one embodiment, the measured voltage drop signal has two sinusoidal voltage signals, which can be expressed as a first sinusoidal voltage signal $b_1 \cdot \sin(n_1 wt)$, a second sinusoidal voltage signal $b_2 \cdot \sin(n_2 wt)$, respectively.

As shown in FIG. 11, in a certain embodiment, the voltage drop signal measured in the device 606 is transmitted to a processor 608. The processor 608 has signal multiplier 610-1, 610-2, and integrators 612-1, 612-2. The sinusoidal current signals, $\sin(n_1 wt)$ and $\sin(n_2 wt)$, are transmitted from the signal generators 602-1, 602-2 to the multiplier 610-1, 610-2, respectively. In the multiplier 610-1, the voltage drop signal is multiplied by the first sinusoidal current signal, and then the multiplied signal is integrated for a predetermined period in the integrator 612-1.

Accompanying equations, one embodiment for processing a voltage drop signal will be discussed. The voltage drop signal can be expressed using sinusoidal voltage signals as follows:

$$g(t) = b_1 \times f_1(t) + b_2 \times f_2(t),$$

wherein $$f_1(t) = \sin(n_1 wt), \text{ and } f_2(t) = \sin(n_2 wt)$$

where, $n_2 = k \cdot n_1$, and k is an integer.

The result of multiplying g(t) by $f_1(t)$ in the multiplier 610-1 and subsequent integrating the multiplied signal for a time period which is the period $T_1$ of g(t) in the integrator 612-1 is given by:

$$\int g(t) \times f_1(t) dt = \int b_1 \times f_1(t) \times f_1(t) dt + \int b_2 \times f_2(t) \times f_1(t) dt$$

$$= \int b_1 \times \sin(n_1 wt) \times \sin(n_1 wt) dt +$$

$$\int b_2 \times \sin(n_2 wt) \times \sin(n_1 wt) dt$$

$$= \frac{1}{2} \int b_1 \times (1 - \cos(2n_1 wt)) dt +$$

$$\frac{1}{2} \int b_2 \times \{\cos(n_2 - n_1) wt - \cos(n_2 + n_1) wt\} dt$$

$$= b_1 \times T_1 / 2$$

since $$\int (1 - \cos(2n_1 wt)) dt = T_1, \text{ and}$$

$$\int \{\cos(n_2 - n_1) wt - \cos(n_2 + n_1) wt\} dt = 0$$

The processor 608 can further compute an impedance value of a body segment, in the illustrated embodiment, for example, the trunk of the body 10, with respect to the first frequency of sinusoidal current signal using an equation, for example, $$Z_{first\,frequency} = b_1 / c_1$$

In the multiplier 610-2, the voltage drop signal is multiplied by the second sinusoidal current signal, and then the multiplied signal is integrated for a predetermined period in the integrator 612-2. Similarly, from the result of multiplying g(t) by $f_2(t)$ in the multiplier 610-2 and subsequent integrating the multiplied signal for a time period which is the period $T_1$ of g(t) in the integrator 612-2.

In one embodiment, the phase of a voltage drop signal can be shifted from that of a sinusoidal current signal which is to be multiplied in the voltage drop signal. The amount of the phase shift can be analyzed using signal transformation process, for example, fast Fourier transform (FFT). The phase-shifted waveform of the sinusoidal current can be multiplied.

In some embodiments, a voltage drop signal can be multiplied by each of a plurality of phase-shifted waveforms of a sinusoidal current signal in a multiplier, for example, the multiplier 610-1 to obtain a plurality of multiplied signals. The plurality of phase-shifted waveforms have substantially same amplitude value and same period, but the phases of the waveforms are different from one another. For each of the plurality of multiplied signals, the multiplied signal is integrated for a predetermined period in the integrator, for example, the integrator 612-1. Through this convolution process, a plurality of integrated values are obtained. In one embodiment, among the plurality of integrated values, the greatest one is selected to calculate an impedance value. Generally, when the number of phase-shifted waveforms in one convolution process is smaller than the number of phase-shifted waveforms in another convolution process, the other convolution process can provide a more accurate result, but takes more time to obtain the result.

Mixed Current Signal of Modulated Signals

Figure 12:
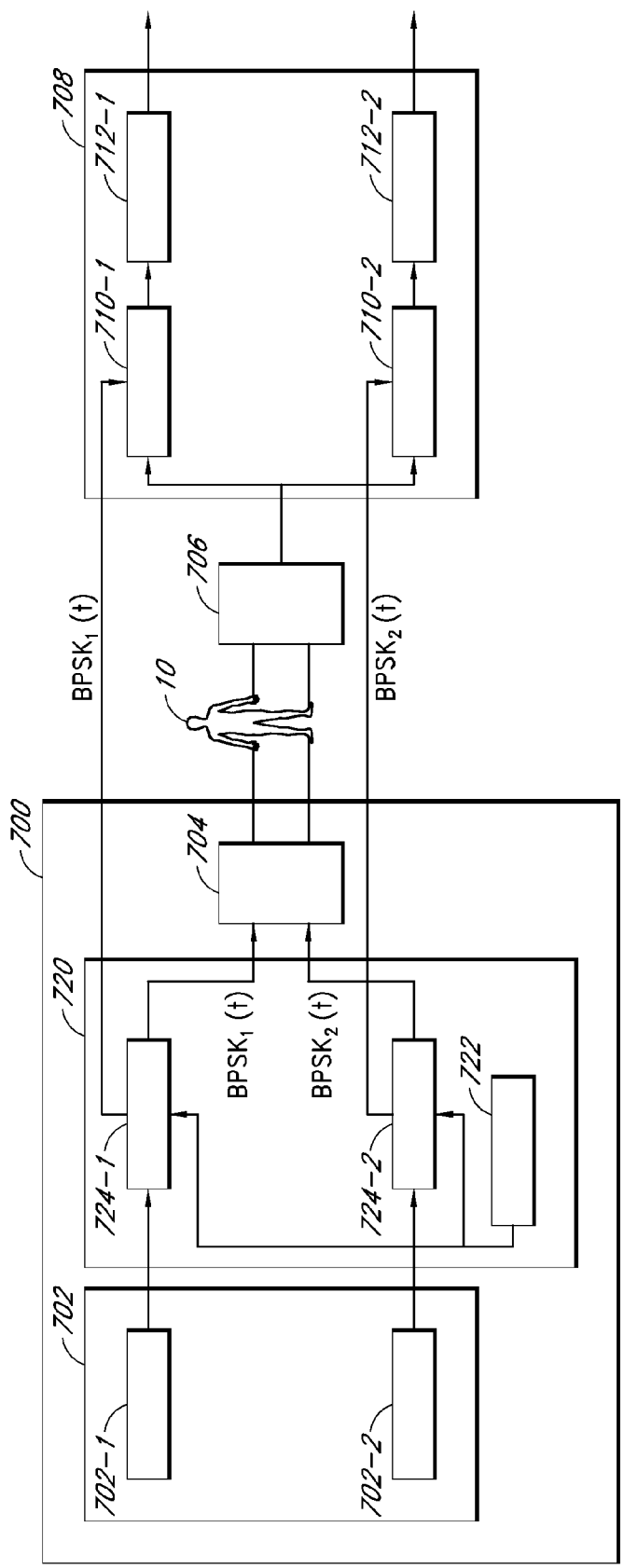
FIG. 12 is a block diagram of a body composition analyzer using a mixed modulated signal of multiple frequencies in accordance with one embodiment.

In one embodiment, as shown in FIG. 12, a current device 700 can include sinusoidal current signal generators 702-1, 702-2 and a signal modulator 720. The signal modulator 720 has a code generator 722 configured to generate a modulation code to be used in modulation procedure, for example, a PN code. In one embodiment, the modulation code can be a code that is artificially generated or manipulated to be substantially distinguishable from a noise or other signals which are naturally generated. The modulator 720 further has signal multipliers 724-1, 724-2.

A sinusoidal current signal having a first frequency is generated in the generator 702-1, and another sinusoidal current signal having a second frequency is generated in the generator 702-2, respectively. In one embodiment, a PN code is generated in the code generator 722. Each sinusoidal current signal is multiplied by the PN code in each of the multipliers 724-1, 724-2 to generate a modulated signal, and then the modulated signals is transmitted to an adder 704 to form a combined current signal. In the illustrated embodiment, the current signal is modulated with a binary phase-shifting keying (BPSK) modulation scheme. In other embodiments, however, other modulation scheme, for example, another phase-shifting keying modulation scheme, orthogonal frequency division multiplexing (OFDM), etc can be used.

Referring to FIGS. 13A-13C, in a certain embodiment, the sinusoidal current signal generator 702-1 generates a sinusoidal signal shown in FIG. 13A. The PN code generator 722 generates, for example, a PN code as shown in FIG. 13B. The sinusoidal signal and the PN code are multiplied in the signal multiplier 724-1 to generate, for example, a modulated signal as shown in FIG. 13C, but not limited thereto.

Referring back to FIG. 12, the combined signal is applied to the human body 10, and a voltage drop signal can be measured in the same manner discussed above. The voltage drop signal between two points of the body 10 is measured by a voltage measuring device 706. In one embodiment, the measured voltage drop signal has two modulated voltage signals having different frequencies.

As shown in FIG. 12, in a certain embodiment, the voltage drop signal measured in the device 706 transmitted to a processor 708. The processor 708 has signal multipliers 710-1, 710-2, and integrators 712-1, 712-2. The modulated current signals, $BPSK_1(t)$ and $BPSK_2(t)$, are transmitted from the signal modulators 724-1, 724-2 to the multipliers 710-1, 710-2, respectively.

The voltage drop signal is multiplied by the modulated current signal $BPSK_1(t)$ at the multiplier 710-1, and then the multiplied signal is integrated in the integrator 712-1. Similarly, the voltage drop signal is multiplied by the modulated current signal $BPSK_2(t)$ at the multiplier 710-2, and then the multiplied signal is integrated in the integrator 712-2. Similarly to the embodiment illustrated FIG. 11, the integrated values obtained in the integrators 712-1, 712-2 can be used for calculate impedances values of the body segment, in the illustrated embodiment, for example, the trunk of the body 10, for the first and second frequencies, respectively. The use of modulated signals can be advantageous as the calculated impedance value does not include influence of an unwanted noise. In a certain circumstance, measured voltage drop signals may include an influence of an unwanted noise. By using the modulated signal and process the measured voltage signals as discussed above, the influence of the noise can be properly removed.

In at least some of the aforesaid embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of analyzing composition of a body, the method comprising:
   establishing contact of current electrodes with four extremities, each extremity contacting at least one of the current electrodes;
   establishing contact of voltage measuring electrodes with the four extremities, each extremity contacting at least one of the voltage measuring electrodes;
   applying a first current signal between first and second extremities through a body via the current electrodes contacting the first and second extremities;
   simultaneously with applying of the first current signal, applying a second current signal between third and fourth extremities through the body via the current electrodes contacting the third and fourth extremities;
   simultaneously measuring voltage signals from the voltage measuring electrodes contacting the four extremities; and
   processing a first set of voltage signals among the measured voltage signals to determine a composition parameter of a first portion of the body based on the first set of voltage signals and the first current signal, and further processing a second set of voltage signals among the measured voltage signals to determine a composition parameter of a second portion of the body based on the second set of voltage signals and the second current signals, wherein the composition of the body is assessed using at least the determined composition parameters,
   wherein the first current signal comprises a first sinusoidal signal having a first frequency and a second sinusoidal signal having a second frequency which is distinguishable from the first frequency, wherein the first current signal represents superimposed frequencies,
   wherein the composition parameter of the first portion comprises a first value representing impedance of the first portion with respect to the first frequency and a second value representing impedance of the first portion with respect to the second frequency.

2. The method of claim 1, wherein the voltage signals are measured while the first and second current signals are applied.

3. The method of claim 1, wherein the first current signal is applied using a first current source and the second current signal is applied using a second current source which is decoupled from the first current source.

4. The method of claim 1, wherein the first set of voltage signals are measured in response to the application of the first current signal.

5. The method of claim 1, wherein said processing the first set of voltage signals comprises:
   selecting two voltage signals from the first set of voltage signals; and
   determining a voltage drop signal using the selected voltage signals;
   wherein the composition parameter of the first portion is determined based on the voltage drop signal and the first current signal.

6. The method of claim 1, wherein the composition parameter comprises a value representing impedance of the first portion.

7. The method of claim 1, wherein the composition parameter comprises at least one selected from the group consisting of percentages of body water, body fat, bone, and muscle.

8. The method of claim 1, wherein said applying the first current signal comprises generating a modulated signal to be applied.

9. The method of claim 1, wherein said applying the first current signal comprises:
   generating a first modulated signal having a first waveform;
   generating a second modulated signal having a second waveform distinguishable from the first waveform; and
   combining the first and second modulated signals to form the first current signal.

10. The method of claim 1, wherein the first current signal represents a single frequency.

11. The method of claim 10, wherein applying the first current signal comprises generating a modulated signal representing the single frequency.

12. The method of claim 11, wherein said modulated signal is generated using a phase-shifting keying (PSK) modulation scheme.

13. The method of claim 1, wherein the first extremity is one arm of the body and the second extremity is one leg of the body.

14. The method of claim 1, wherein the first portion of the body comprises at least one selected from a right arm, a left arm, a right leg, a left leg and a trunk.

15. A method of analyzing composition of a body, the method comprising:
   establishing contact of current electrodes with four extremities, each extremity contacting at least one of the current electrodes;

establishing contact of voltage measuring electrodes with the four extremities, each extremity contacting at least one of the voltage measuring electrodes;

applying a first current signal between first and second extremities through a body via the current electrodes contacting the first and second extremities;

simultaneously with applying of the first current signal, applying a second current signal between third and fourth extremities through the body via the current electrodes contacting the third and fourth extremities;

simultaneously measuring voltage signals from the voltage measuring electrodes contacting the four extremities; and processing a first set of voltage signals among the measured voltage signals to determine a composition parameter of a first portion of the body based on the first set of voltage signals and the first current signal, and further processing a second set of voltage signals among the measured voltage signals to determine a composition parameter of a second portion of the body based on the second set of voltage signals and the second current signals, wherein the composition of the body is assessed using at least the determined composition parameters, wherein the first current signal comprises a first sinusoidal signal having a first frequency and a second sinusoidal signal having a second frequency which is distinguishable from the first frequency, wherein the first current signal represents superimposed frequencies, wherein the second sinusoidal signal is a harmonic of the first sinusoidal signal.

16. The method of claim 1, wherein said process comprises:

selecting two voltage signals from the first set of voltage signals;

determining a voltage drop signal using the two voltage signals; and determining the first and second values based on the voltage drop signal and the first current signal.

17. The method of claim 16, wherein processing the voltage drop signal comprises:

multiplying a signal having the first frequency to the voltage drop signal to obtain a multiplied signal;

integrating the multiplied signal for a period to obtain an integrated value; and processing the integrated value to determine the first value.

18. The method of claim 9, wherein each of said modulated signals is generated using a phase-shifting keying (PSK) modulation scheme.

* * * * *